United States Patent
Orbay et al.

(10) Patent No.: US 10,251,757 B2
(45) Date of Patent: *Apr. 9, 2019

(54) GROOVED SLOT ALLOWING ADJUSTMENT OF THE POSITION OF A BONE FIXATION DEVICE FOR OSTEOSYNTHESIS

(71) Applicant: SKELETAL DYNAMICS, LLC, Miami, FL (US)

(72) Inventors: Jorge L. Orbay, Miami, FL (US); Thomas Norman, Miami, FL (US); Juan Salcedo, Miami, FL (US); Alexander Gil, Miami, FL (US)

(73) Assignee: Skeletal Dynamics LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,714

(22) Filed: Nov. 17, 2017

(65) Prior Publication Data

US 2018/0071105 A1 Mar. 15, 2018

Related U.S. Application Data

(60) Continuation-in-part of application No. 14/815,332, filed on Jul. 31, 2015, now Pat. No. 9,820,862, which
(Continued)

(51) Int. Cl.
*A61B 17/72* (2006.01)
*A61F 2/42* (2006.01)
(Continued)

(52) U.S. Cl.
CPC ........ *A61F 2/4261* (2013.01); *A61B 17/1782* (2016.11); *A61B 17/72* (2013.01);
(Continued)

(58) Field of Classification Search
CPC ........ A61B 17/72–17/748; A61B 17/84–17/86
See application file for complete search history.

(56) References Cited

U.S. PATENT DOCUMENTS

| 526,580 A | 9/1894 | Osyor |
| 781,571 A * | 1/1905 | Thomas ................. F16B 37/02 411/437 |

(Continued)

FOREIGN PATENT DOCUMENTS

| WO | 9602202 A1 | 2/1996 |
| WO | 2007009123 A2 | 1/2007 |

*Primary Examiner* — Eduardo C Robert
*Assistant Examiner* — Michelle C Eckman
(74) *Attorney, Agent, or Firm* — Laurence A. Greenberg; Werner H. Stemer; Ralph E. Locher

(57) ABSTRACT

A grooved slot is provided in a bone fixation device for osteosynthesis that permits adjustment of the bone fixation device relative to the bone, before the bone fixation device is finally fixed to the bone. The grooves are formed on the two longitudinally extending, facing walls of the slot, with the grooves on a first side wall of the slot having a vertical displacement of exactly one-half pitch relative to the grooves on the second, opposite side wall of the slot.

13 Claims, 19 Drawing Sheets

Related U.S. Application Data is a division of application No. 12/561,805, filed on Sep. 17, 2009, now Pat. No. 9,095,440, application No. 15/816,714, which is a continuation-in-part of application No. 13/604,931, filed on Sep. 6, 2012, which is a continuation-in-part of application No. 13/366,886, filed on Feb. 6, 2012, now Pat. No. 8,814,918, application No. 15/816,714, which is a continuation-in-part of application No. 14/260,833, filed on Apr. 24, 2014.

(60) Provisional application No. 61/536,316, filed on Sep. 19, 2011, provisional application No. 61/531,485, filed on Sep. 6, 2011, provisional application No. 61/239,277, filed on Sep. 2, 2009, provisional application No. 61/097,616, filed on Sep. 17, 2008, provisional application No. 61/815,634, filed on Apr. 24, 2013.

(51) Int. Cl.
*A61B 17/17* (2006.01)
*A61F 2/30* (2006.01)

(52) U.S. Cl.
CPC ...... *A61B 17/7241* (2013.01); *A61B 17/7283* (2013.01); *A61B 17/7291* (2013.01); *A61B 17/1717* (2013.01); *A61B 17/1725* (2013.01); *A61B 17/7225* (2013.01); *A61F 2002/3054* (2013.01); *A61F 2002/30062* (2013.01); *A61F 2002/30331* (2013.01); *A61F 2002/30481* (2013.01); *A61F 2002/30507* (2013.01); *A61F 2002/30538* (2013.01); *A61F 2002/30622* (2013.01); *A61F 2002/30774* (2013.01); *A61F 2002/30777* (2013.01); *A61F 2002/4264* (2013.01); *A61F 2210/0004* (2013.01); *A61F 2220/0025* (2013.01); *A61F 2220/0033* (2013.01); *A61F 2250/0006* (2013.01)

(56) References Cited

U.S. PATENT DOCUMENTS

| | | | |
|---|---|---|---|
| 1,375,781 A * | 4/1921 | De Long | F16B 37/0878 |
| | | | 269/240 |
| 3,744,488 A | 7/1973 | Cox | |
| 4,106,128 A | 8/1978 | Greenwald et al. | |
| 4,259,752 A | 4/1981 | Taleisnik | |
| 5,074,731 A * | 12/1991 | Schneider | B23G 1/32 |
| | | | 411/310 |
| 5,108,398 A | 4/1992 | McQueen et al. | |
| 5,352,227 A * | 10/1994 | O'Hara | A61B 17/72 |
| | | | 606/62 |
| 5,489,284 A * | 2/1996 | James | A61B 17/1717 |
| | | | 606/62 |
| 5,505,734 A * | 4/1996 | Caniggia | A61B 17/7225 |
| | | | 606/63 |
| 5,620,445 A * | 4/1997 | Brosnahan | A61B 17/72 |
| | | | 606/62 |
| 5,626,580 A * | 5/1997 | Brosnahan | A61B 17/72 |
| | | | 606/62 |
| 5,709,686 A * | 1/1998 | Talos | A61B 17/8014 |
| | | | 606/280 |
| 5,855,579 A | 1/1999 | James et al. | |
| 6,652,528 B2 | 11/2003 | Vandewalle | |
| 6,808,527 B2 | 10/2004 | Lower | |
| 7,001,386 B2 | 2/2006 | Sohngen et al. | |
| 7,338,246 B2 * | 3/2008 | Caspi | F16B 37/0892 |
| | | | 411/432 |
| 7,780,664 B2 * | 8/2010 | Orbay | A61B 17/1725 |
| | | | 606/62 |
| 2002/0103488 A1 | 8/2002 | Lower et al. | |
| 2005/0055023 A1 | 3/2005 | Sohngen et al. | |
| 2005/0096656 A1 | 5/2005 | Behrens | |
| 2005/0102031 A1 | 5/2005 | Leonard | |
| 2005/0277937 A1 * | 12/2005 | Leung | A61B 17/8057 |
| | | | 606/287 |
| 2006/0058797 A1 * | 3/2006 | Mathieu | A61B 17/8047 |
| | | | 606/54 |
| 2006/0264946 A1 * | 11/2006 | Young | A61B 17/1728 |
| | | | 606/915 |
| 2007/0055251 A1 | 3/2007 | Huebner et al. | |
| 2007/0123873 A1 * | 5/2007 | Czartoski | A61B 17/72 |
| | | | 606/62 |
| 2007/0123878 A1 * | 5/2007 | Shaver | A61B 17/72 |
| | | | 606/64 |
| 2008/0051791 A1 * | 2/2008 | Young | A61B 17/8014 |
| | | | 606/250 |
| 2008/0183171 A1 | 7/2008 | Elghazaly et al. | |
| 2008/0221577 A1 * | 9/2008 | Elghazaly | A61B 17/7241 |
| | | | 606/64 |
| 2008/0234749 A1 * | 9/2008 | Forstein | A61B 17/8057 |
| | | | 606/291 |
| 2009/0171399 A1 * | 7/2009 | White | A61B 17/80 |
| | | | 606/286 |
| 2009/0228007 A1 | 10/2009 | Justin et al. | |
| 2009/0306664 A1 * | 12/2009 | Teeny | A61B 17/725 |
| | | | 606/64 |
| 2010/0130978 A1 * | 5/2010 | Orbay | A61B 17/7241 |
| | | | 606/62 |
| 2010/0312286 A1 * | 12/2010 | Dell'Oca | A61B 17/8057 |
| | | | 606/291 |
| 2011/0218531 A1 * | 9/2011 | Orbay | A61B 17/56 |
| | | | 606/62 |
| 2012/0022534 A1 * | 1/2012 | Orbay | A61B 17/7241 |
| | | | 606/62 |
| 2018/0071105 A1 * | 3/2018 | Orbay | A61B 17/7283 |

* cited by examiner

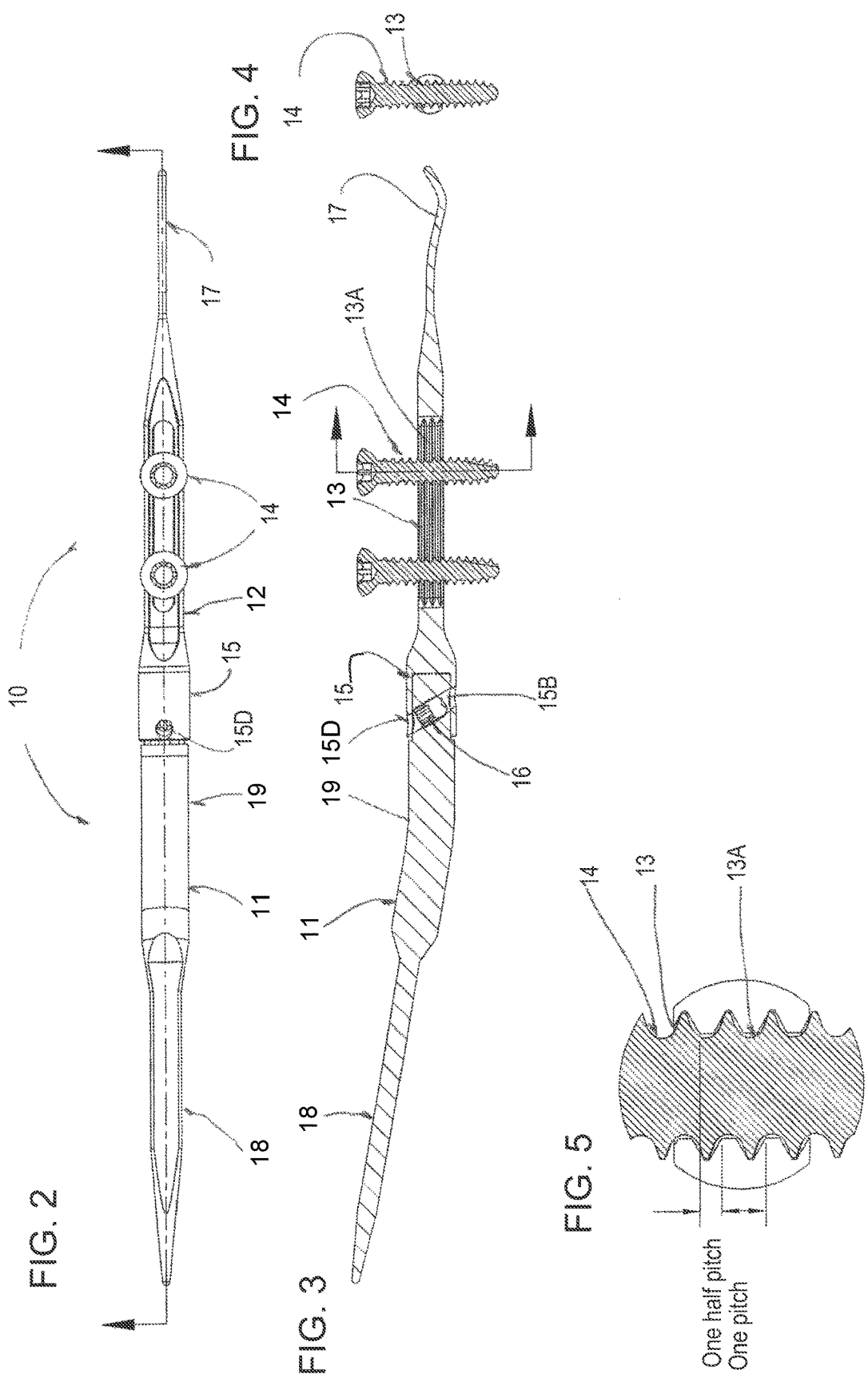

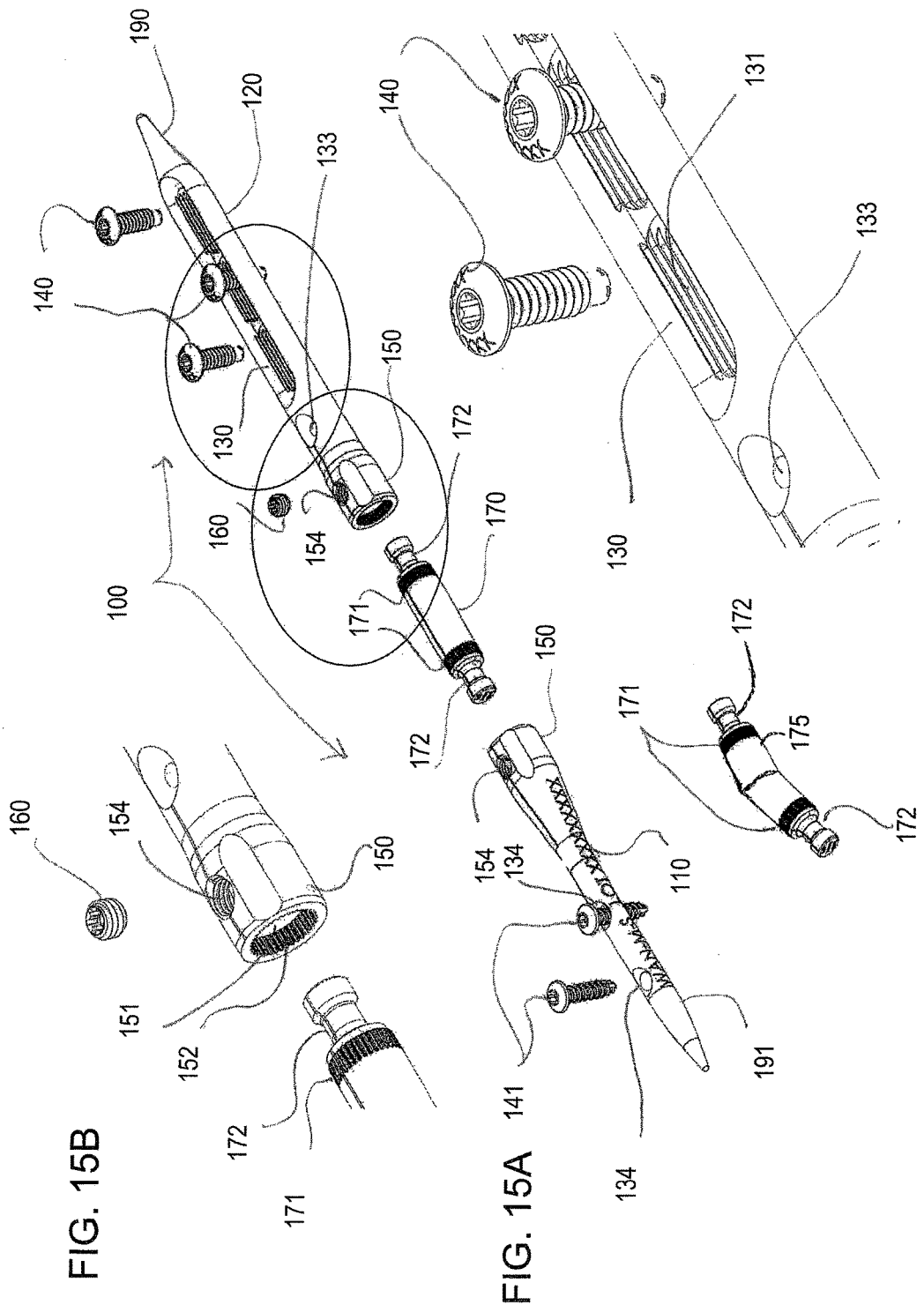

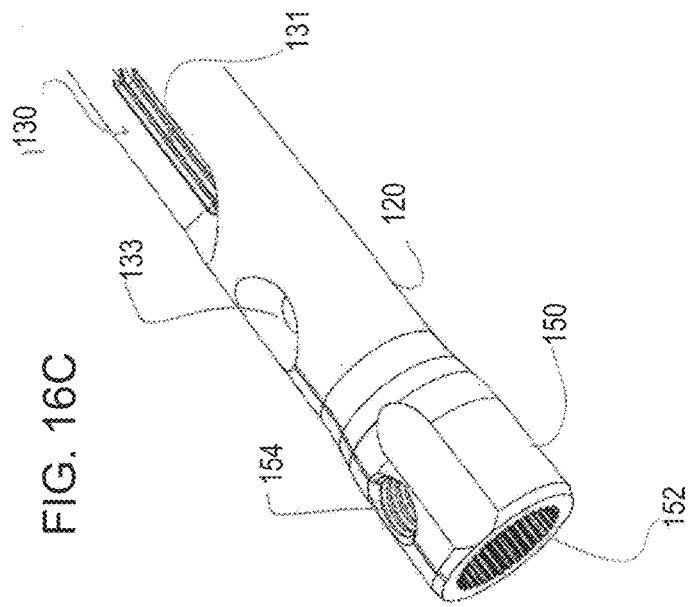
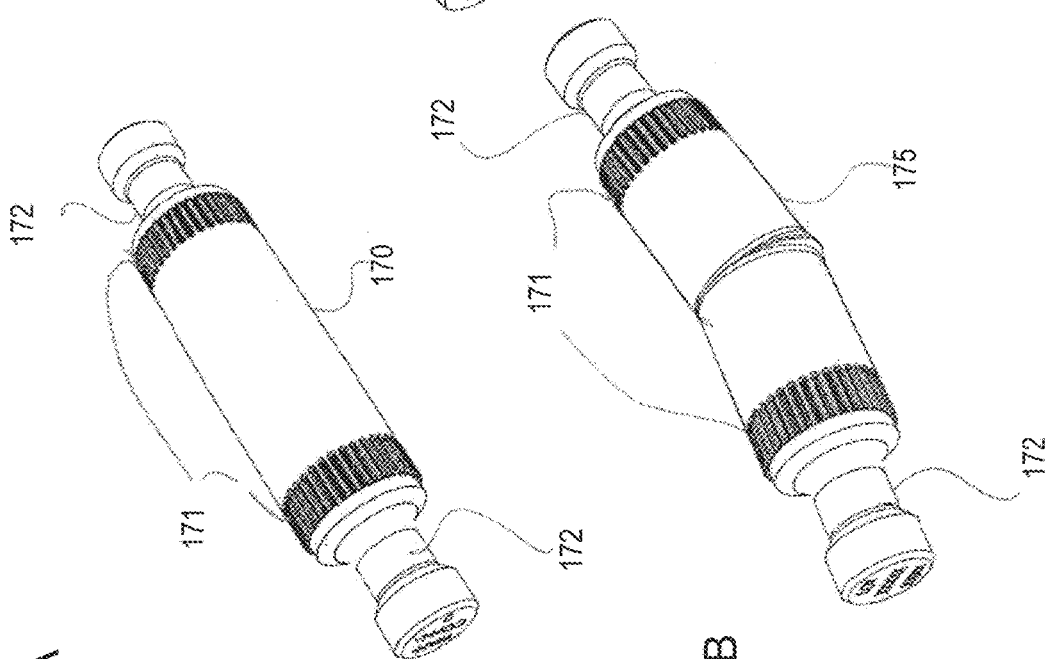

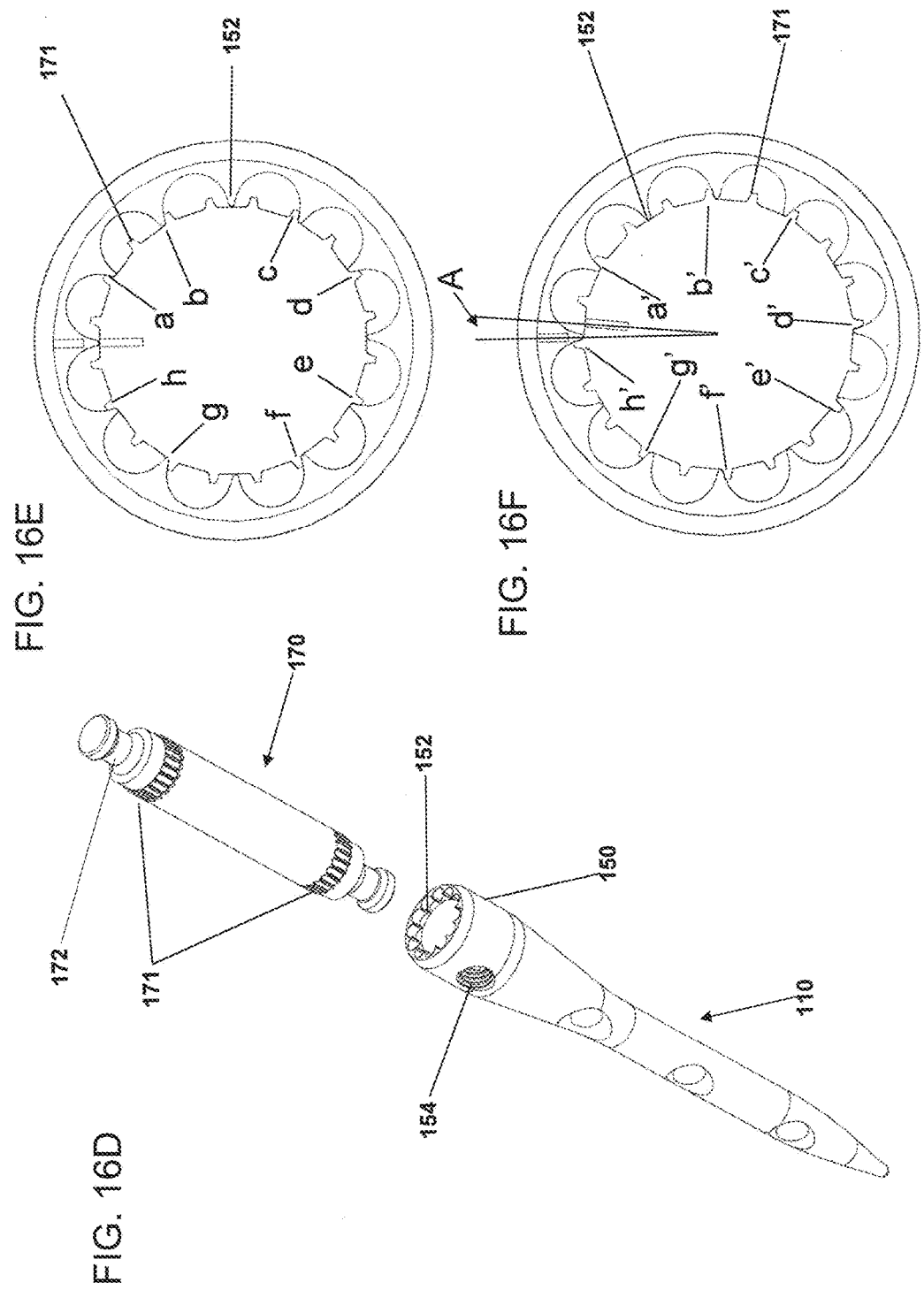

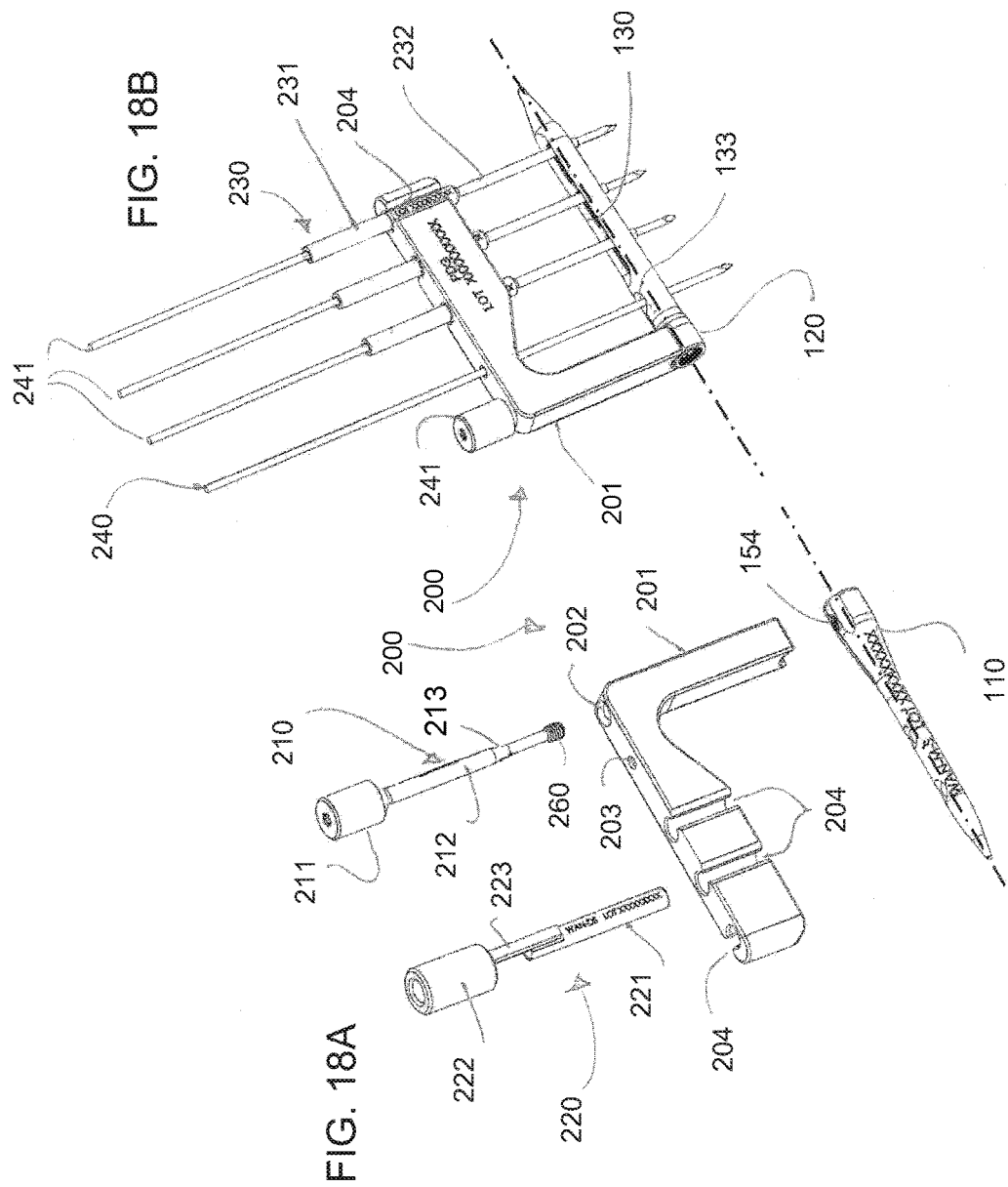

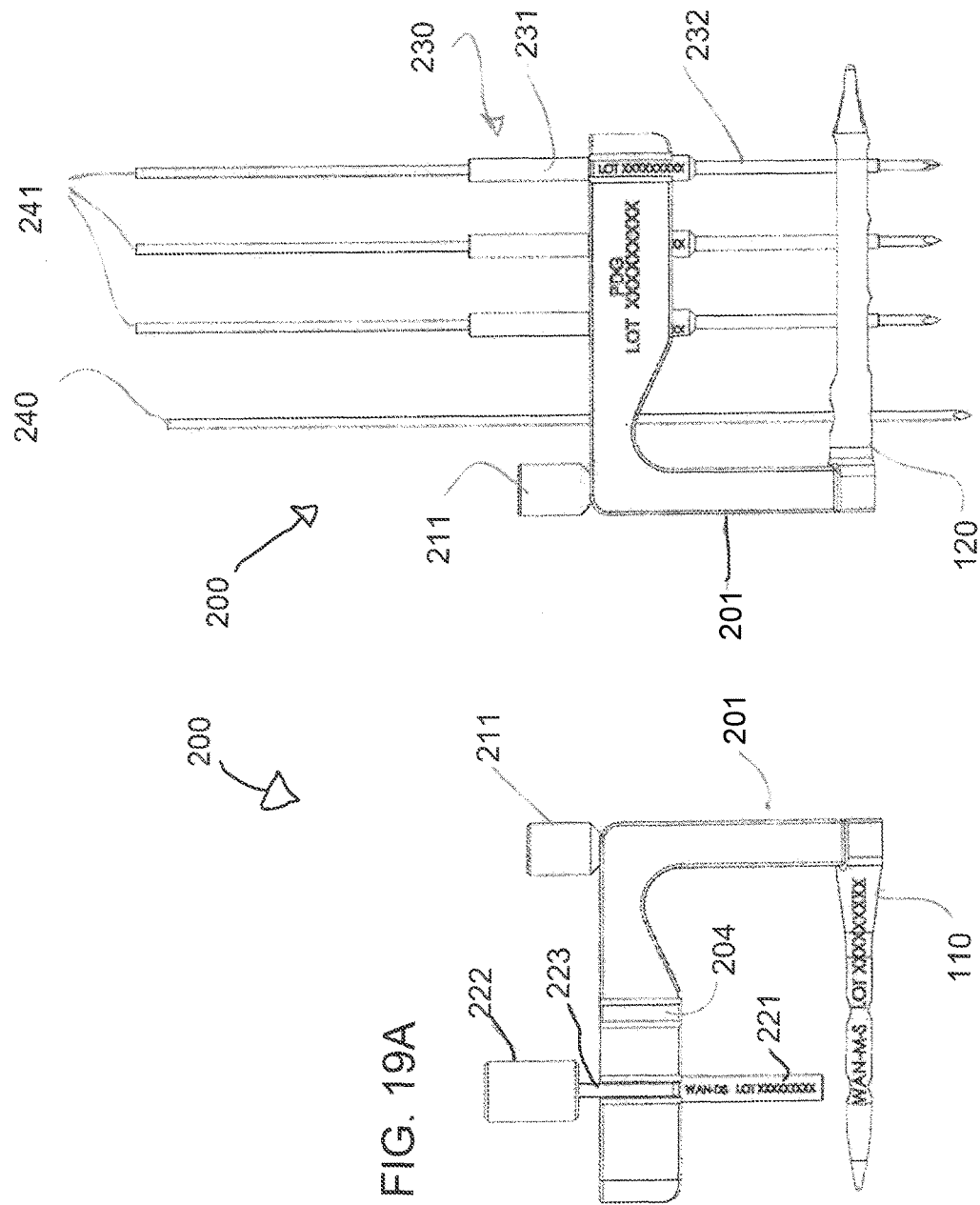

GROOVED SLOT ALLOWING ADJUSTMENT OF THE POSITION OF A BONE FIXATION DEVICE FOR OSTEOSYNTHESIS

CROSS-REFERENCE TO RELATED APPLICATIONS

The present application is a Continuation-in-Part of U.S. patent application Ser. No. 14/815,332, filed on Jul. 31, 2015, issuing on Nov. 21, 2017 as U.S. Pat. No. 9,820,862, which application was a divisional of U.S. patent application Ser. No. 12/561,805, filed on Sep. 17, 2009, now U.S. Pat. No. 9,095,440, which claimed priority to: Provisional Patent Application No. 61/097,616, filed on Sep. 17, 2008 and Provisional Patent Application No. 61/239,277, filed on Sep. 2, 2009; the present application additionally claims priority to co-pending U.S. patent application Ser. No. 13/604,931, filed on Sep. 6, 2012, which claimed priority to U.S. patent application Ser. No. 13/366,886, now U.S. Pat. No. 8,814,918, which claimed priority to: Provisional Patent Application No. 61/531,485, filed on Sep. 6, 2011, Provisional Patent Application No. 61/536,316, filed on Sep. 19, 2011 and Provisional Patent Application No. 61/595,986, filed on Feb. 7, 2012; the present application further claims priority to co-pending U.S. patent application Ser. No. 14/260,833, filed on Apr. 24, 2014, which claimed priority to Provisional Patent Application No. 61/815,634, filed on Apr. 24, 2013; all of the above-named applications being incorporated herein, by reference, in their entireties.

FIELD OF THE INVENTION

The instant invention relates to a grooved slot for incorporation into a bone fixation device for osteosynthesis, which slot permits movement and adjustment of the bone fixation device, intraoperatively, prior to fixation, and to a bone fixation device including the described grooved slot.

BACKGROUND OF THE INVENTION

Arthrodesis or joint fusion is a well known procedure for osteosynthesis often associated with the spine, the ankle or the wrist. In particular, the wrist or carpus is the complex joint between the forearm and the hand. It allows the hand three degrees of movement important to manual dexterity: flexion/extension in the palmar-dorsal plane; adduction/abduction, also referred to as radial or ulnar deviation, in the medial-lateral plane and circumduction, the combination of both movements. These degrees of movement combine with the degrees of movement provided by the forearm (pronation/supination), the elbow (flexion/extension) and those of the shoulder to give the hand a vast positional range.

Wrist arthropathy occurs when the wrist joint becomes diseased as a result of trauma, osteoarthritis (OA) or rheumatoid arthritis (RA) among other causes. In wrist arthropathy, movement of the wrist causes severe pain that makes the patient hesitant to use the affected hand, thereby creating a substantial degree of disability. The pain in wrist arthropathy is the result of motion-exacerbated irritation of afferent nerves within the wrist bones resulting from inflammation or from bone-on-bone contact that follows degeneration of articular cartilage.

The treatment of wrist arthropathy centers upon balancing two contradictory objectives: relieving motion induced pain while attempting to retain as much motion as possible.

Medically, the most common treatment of arthropathy relies on the use of nonsteroidal anti-inflammatory drugs (NSAIDs) that relieve pain without affecting motion. Corticosteroids, sometimes combined with anesthetic, are also used to alleviate pain but the results are almost always transient. Conservatively, forced rest by applying removable external splints that temporarily limit motion is often useful but, if overused, can lead to subsequent stiffness or weakness from the immobilization.

Several surgical approaches have been developed to alleviate pain while attempting to preserve motion to the greatest degree possible. In some cases, partial denervation of the wrist can reduce pain and may allow postponement of more immobilizing procedures. Wrist arthroplasty (replacement) has evolved considerably in the last decades and may be a preferred procedure in some patients because it preserves a less painful, albeit decreased range of motion.

Wrist arthrodesis is performed to relieve intractable pain that cannot be relieved by conservative or medical treatment and, sometimes, after failed denervation or arthroplasty. Wrist arthrodesis is an established surgical technique to join (fuse) adjacent bones in the wrist by rigidly positioning them at their articular surfaces. By maintaining this placement, sometimes in the presence of bone graft, bone cell growth is stimulated, causing the bones to fuse together. Once the bones fuse, all motion that existed at the worn joint surfaces ceases and the pain caused by the irritation of the afferent nerves is significantly reduced or eradicated.

In limited or partial wrist arthrodesis a selected group of wrist bones are fused. Variations of the procedure such as triscaphe, radioscaphoid, radiolunate, scapholunatecapitate and four-corner fusion attempt to alleviate pain by fusing those articulations determined or suspected of originating pain and may be indicated, among others, in patients that require intricate use of their hands because more residual motion of the wrist can be preserved. The trade-off is that only rarely does the procedure result in full relief of pain.

Total wrist arthrodesis is very effective in relieving pain but all three wrist motions are permanently lost, thereby reducing manual dexterity. The trade-off, on the positive side, is that the elimination of pain permits the recovery of finger mobility and a relatively strong grip which, previously, would have been compromised by pain.

Fracture fixation is another form of osteosynthesis, involving the reduction and internal fixation of a bone fracture with an implantable device. In contrast to arthrodesis of a joint, discussed above, fracture fixation unites the ends of a fractured bone by mechanical means, such as a bone plate.

DESCRIPTION OF THE RELATED ART

Total wrist arthrodesis typically involves the fusion of the radius, one metacarpal bone (usually the third) and some of the carpal bones. Sometimes, typically in cases of inflammatory arthritis, it can be achieved with Steinmann pin fixation. Most frequently, it is achieved by the use of a plate implant affixed to the dorsal surfaces of these bones. The rigidity of the plate facilitates bone fusion and obviates the prolonged use of cast immobilization, permitting earlier post-operative rehabilitation with the consequential accelerated recovery of finger motion and grip. Although adaptation to the immobilized wrist is required, many patients are able to accomplish their daily tasks without major problems.

An example of a frequently used total wrist arthrodesis dorsal plate is described in "The Wrist Fusion Set" by Synthes®. This plate is strap-like and pre-contoured in the palmar-dorsal plane, while straight in the medial-lateral plane. It is normally attached with multiple screws to the dorsal aspect of one of the metacarpal bones, multiple screws to the dorsal aspect of the radius and, often, one screw to the capitate.

A refinement of the dorsal plate is disclosed in U.S. Pat. No. 5,853,413 to Carter (the "'413 patent"). In discussing a strap-like plate device, such as the Synthes device, lines 23-32 of col. 1 of the '413 patent states: "Since the anatomical axis of the third metacarpal is not disposed in alignment with the anatomical axis of the radius in the medial-lateral direction, it is thus necessary to place the strap-like fusion plate at an angle extending between the radius and third metacarpal, relative to the anatomical axes of the radius and third metacarpal". To address this perceived problem, the '413 patent discloses using a plate having offset distal and proximal ends, such that the distal end and the proximal end can be placed substantially parallel to the anatomical axes of the third metacarpal and the radius, respectively.

Col. 4 of the '413 patent, lines 58-60, disclose that various sizes and styles of plates can be made available to accommodate different angles and offsets D, as well as to vary other sizing and design features, as desired.

Additionally, plates and other bone fixation devices have been used in fracture fixation, as well as arthrodesis.

What is needed is a bone fixation device for osteosynthesis, the placement of which can be easily adjusted by a surgeon, intraoperatively, during fixation.

SUMMARY OF THE INVENTION

It is accordingly an object of this invention to provide a grooved slot in a bone fixation device for osteosynthesis that permits adjustment of the bone fixation device relative to the bone, before the bone fixation device is finally fixed to the bone.

In accordance with one particular embodiment of the invention, at least one slot disposed through the body of a bone fixation device includes grooves formed on the two longitudinally extending, facing walls of the slot, with the grooves on a first side wall of the slot having a vertical displacement of exactly one-half pitch relative to the grooves on the second, opposite side wall of the slot.

In one particular embodiment of the invention, the slotted bone fixation device is used to perform arthrodesis. In another embodiment of the invention, the slotted bone fixation device is used to perform fracture fixation.

Although the invention is illustrated and described herein as embodied in a grooved slot allowing adjustment of a position of a bone fixation device and/or a bone fixation device including such a grooved slot, it is nevertheless not intended to be limited to the details shown, since various modifications and structural changes may be made therein without departing from the spirit of the invention and within the scope and range of equivalents of the claims.

The construction of the invention, however, together with the additional objects and advantages thereof will be best understood from the following description of the specific embodiments when read in connection with the accompanying drawings.

BRIEF DESCRIPTION OF THE DRAWINGS

FIG. 2 is a plan view of the intramedullary arthrodesis nail of FIG. 1

FIG. 3 is a side cross-sectional view of the intramedullary arthrodesis nail of FIGS. 1 and 2.

FIG. 4 is a front cross-sectional view of the screw, the slot and grooved walls of the intramedullary arthrodesis nail of FIG. 3.

FIG. 5 is an enlarged view of a portion of view shown in FIG. 4.

FIG. 15A is an exploded perspective view of a further embodiment of the intramedullary arthrodesis nail including a connector.

FIGS. 15B-15C are partial exploded views of details of the device of FIG. 15A.

FIG. 16A is a perspective view of one particular embodiment of a connector for use in the intramedullary arthrodesis nail of FIG. 15A.

FIG. 16B is a perspective view of another embodiment of a connector for use in the intramedullary arthrodesis nail of FIG. 15A.

FIG. 16C is a partial perspective view of a portion of the intramedullary arthrodesis nail of FIG. 15A.

FIG. 16D is a perspective view of another particular embodiment of a connector and distal nail portions for use in the intramedullary arthrodesis nail of FIG. 15A.

FIG. 16E is a diagrammatic sectional view of the splines of the connector portion and the splines of distal nail portion of FIG. 16D indicating the plurality of engagement points before rotation.

FIG. 16F is a diagrammatic sectional view of the splines of the connector portion and the splines of distal nail portion of FIG. 16D indicating the plurality of engagement points after one step of rotation in the clockwise direction.

FIG. 18A is an exploded perspective view of a drill guide in accordance with one particular embodiment, shown in connection with the installation of the distal nail portion of the intramedullary arthrodesis nail of FIG. 15A and FIG. 18B is a perspective view of the same drill guide, but shown in connection with the installation of the proximal nail portion of the intramedullary arthrodesis nail of FIG. 15A.

FIGS. 19A and 19B are elevational views of the drill guide of FIGS. 18A and 18B in communication with, respectively, the distal nail portion and the proximal nail portion of the intramedullary arthrodesis nail of FIG. 15A.

DETAILED DESCRIPTION OF THE INVENTION

Figure 1:
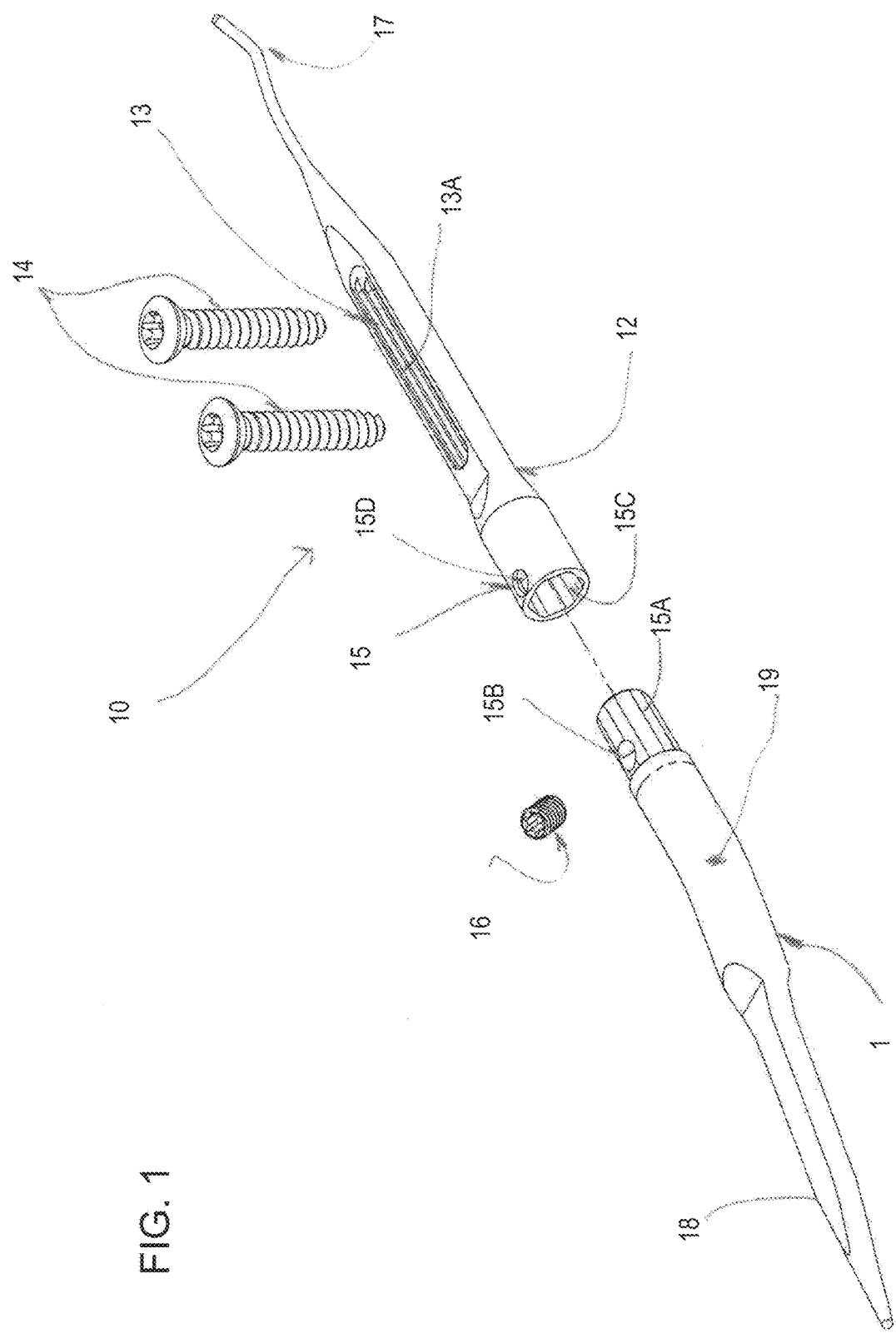
FIG. 1 is an exploded perspective view of a preferred embodiment of an intramedullary arthrodesis nail.

Referring now to the figures of the drawings in detail and more particularly to FIGS. 1, 2 and 3 there is shown one particular embodiment of a multi-part intramedullary arthrodesis nail of the instant invention for performing arthrodesis of the wrist. The intramedullary arthrodesis nail is designed to be placed internally within selected bones of the wrist in order to immobilize the joint during a sufficient period of time to allow the permanent fusion of the selected bones, and in some cases, some adjacent bones of the wrist. The internal placement of the intramedullary arthrodesis nail minimizes incision length, excessive bone resection, tendon damage and persistent tenderness after implantation.

The intramedullary arthrodesis nail shown on FIGS. 1, 2 and 3 is a multi-part device and is preferably made of biocompatible metal (such as titanium, cobalt chrome or stainless steel) or bioabsorbable material (such as PLA or PGA) or a combination of metal and bioabsorbable material. The intramedullary arthrodesis nail 10 includes a distal nail portion 11 intended to be placed, at least partially, within the medullary cavity of at least a first bone and, possibly, a second bone (typically, the third metacarpal and the capitate in the case of the wrist). The distal nail portion 11 includes a body portion 19, preferably formable by bending to allow adjustment of its geometry, a distal tail portion 18, an externally faceted (for example, hexagonal or octagonal) head portion 15a intended to be inserted into a matching internally faceted socket portion 15. Extending through the faceted head 15a is a threaded hole 15b adapted to receive a set screw 16. In the present embodiment, set screw 16 is chosen to be a correspondingly threaded headless set screw, although other types of screws can be used. As more clearly seen in FIG. 3, the axis of threaded hole 15b is oblique in relation to the longitudinal axis of distal nail portion 11 but may also be perpendicular to that axis, as desired.

Referring again to FIGS. 1, 2 and 3, the multi-part intramedullary arthrodesis nail 10 also includes a proximal nail portion 12, intended to be placed, at least partially, within the medullary cavity of at least one other bone of the joint (the radius, in the case of the wrist). The proximal nail portion 12 includes a longitudinal slot 13 with two opposing, grooved parallel side walls 13a. Preferably, at least 2 grooves on each of the two parallel side walls of longitudinal slot 13 are disposed parallel to the longitudinal axis of proximal nail portion 12 and are configured to match the shape and the pitch of the threads of screws 14. As shown more particularly in FIG. 5, in one particular embodiment of the instant invention, the grooves 13a on a first side wall of the slot 13 have a vertical displacement of exactly one-half pitch relative to the grooves on the second, opposite side wall of the slot. This relative displacement of opposite side grooves permits the stable engagement of the threads of screws 14 into the side wall grooves of slot 13 at the tangential contact points of the aforementioned threads with the grooves, while still permitting the loosely engaged screws to be displaced horizontally to any desired position along the length the slot. Complementarily, once the screws are held in a fixed position (for example, by having been inserted into holes drilled in a bone cortex) the slot 13 (and consequently, the totality of proximal nail portion 12) may be displaced longitudinally through a wide range of positions along the axis of the slot, until such time as the surgeon wishes to fix it at a final desired location by further tightening of the screws.

It should be noted that, when screws 14 are tightened by clockwise rotation, such rotation will cause the thread of the screws to pull, draw or lag the grooved longitudinal slot 13 (and consequently, the totality of proximal nail portion 12) towards the heads of the screws. Therefore, any matter that is interposed between the screw heads and the proximal nail portion 12 will be tightly clamped between the aforementioned screw heads and nail.

Figure 13:
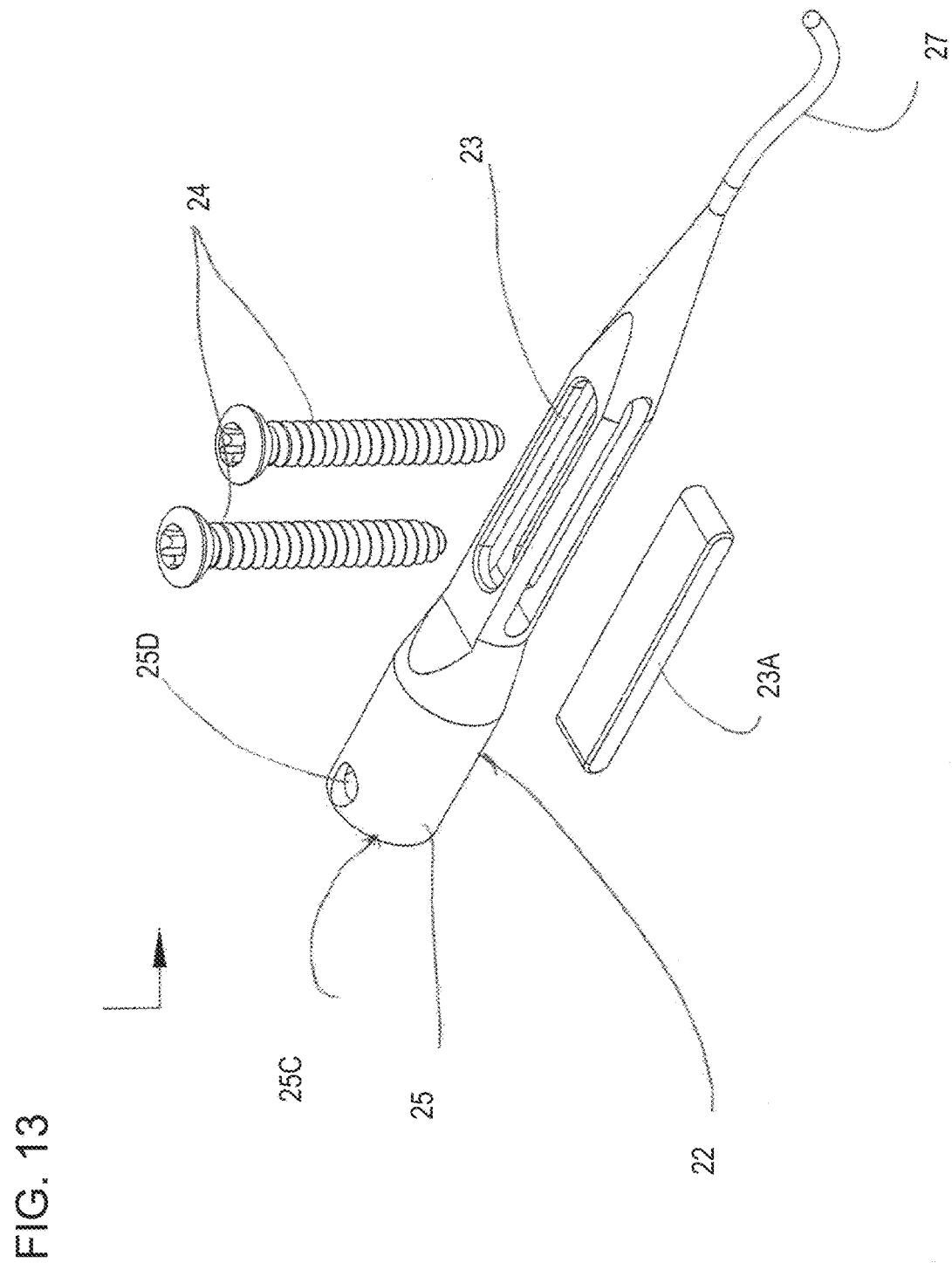
FIG. 13 is an exploded perspective view of an alternate embodiment of the proximal nail portion of the intramedullary arthrodesis nail.

Referring now to FIG. 13, shown therein is an alternate embodiment of a proximal nail portion 22 of an intramedullary arthrodesis nail intended to be placed, at least partially, within the medullary cavity of the radius. The proximal nail portion 22 includes a socket portion 25, a tail portion 27 and a longitudinal slot 23. The longitudinal slot 23 is configured to receive an insert 23a made of a biocompatible plastic material (for example PEEK). The insert 23a is intended provide the same function as the grooved parallel side walls 13a of FIGS. 1 and 3. When screws 24 are held in a fixed position (for example, by having been inserted into holes drilled in the bone cortex) and further partially inserted into slot 23, sufficiently to impede transverse lateral displacement of the slot 23, but without engaging the insert 23a, the aforementioned slot 23 may be displaced longitudinally through a wide range of positions along the axis of the slot until such a time as the surgeon wishes to fix the proximal nail portion 22 at a desired location. This is accomplished by tightening the screws 14, at which time the aforementioned screws will tap into the plastic material and pull, draw or lag the plastic insert (and consequently, the slot 23 and the totality of proximal nail portion 22) towards the head of the screws, firmly clamping any matter interposed between the aforementioned screw heads and the upper surface of proximal nail 22.

Referring now to FIGS. 1, 2, 3 and 13, the proximal nail portion 12, 22 includes an internally faceted (for example hexagonal or octagonal) socket 15, 25 intended to receive a matching externally faceted head portion 15a of the distal nail portion 11. A thru-hole 15d, 25d extends through the outer wall of the socket 15, 25 and opens into the socket 15, 25. Thru-hole 15d, 25d is, in the present embodiment, unthreaded to allow the insertion of set screw 16 into threaded hole 15b, when the head portion 15a is mated with the socket 15, 25. It should be noted that when set screw 16 is fully tightened within threaded hole 15b it engages the lower interior surface of socket 15, 25 in such a way that distal nail portion 11 becomes affixed to proximal nail portion 12, 22, impeding any movement along the longitudinal axis of the nail portions 12, 22. Furthermore, the external facets of head portion 15a simultaneously engage internal facets 15c, 25c located in the sockets 15, 25, thus impeding any rotational motion between distal nail portion 11 and proximal nail portion 12, 22.

Once the set screw 16 has been fully tightened, the distal nail portion 11 and respective proximal nail portion 12, 22 become fully engaged. Thereafter, the locked proximal and distal nail portions 11, 12, 22 will perform structurally as if they were a single, uninterrupted, rigid nail.

Figure 14:
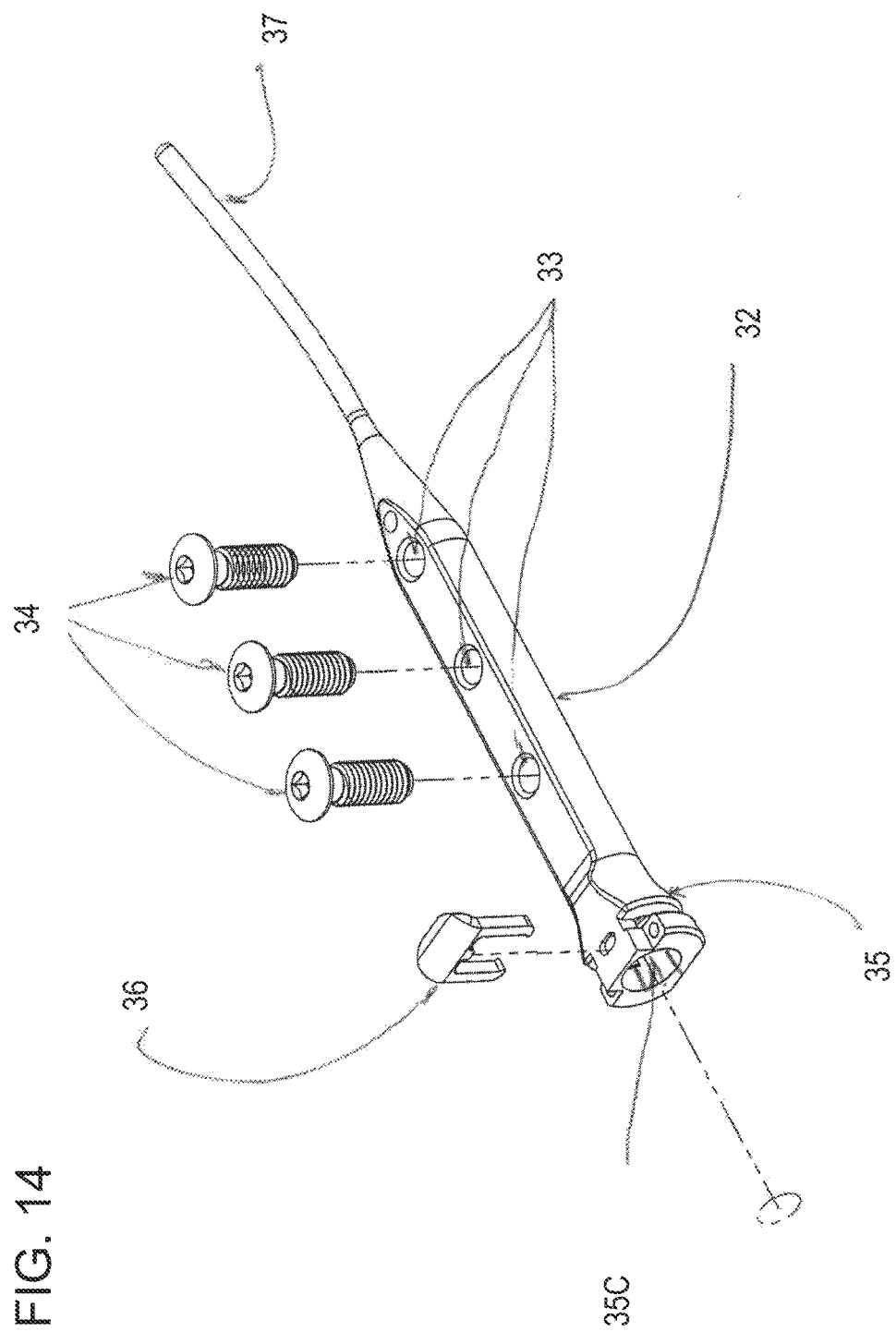
FIG. 14 is an exploded perspective view of a further embodiment of the proximal nail portion of the intramedullary arthrodesis nail.

Referring now to FIG. 14, there is shown an alternate embodiment of a proximal nail portion 32, including a further mechanism for engaging a proximal nail portion 35 to a distal nail portion, such as the distal nail portion 11 of FIG. 1. The proximal nail portion 32 is similar to the proximal nail portions 12, 22 of FIGS. 1 and 13. However, the proximal nail portion 32 does not include a longitudinal slot (13, 23 of FIGS. 1 and 13, respectively). Rather, individual threaded screw holes 33, configured to receive screws 34, as illustrated in FIG. 14, are provided for fixing the proximal nail portion 32 to the bone. Additionally, instead of a set screw, the embodiment of FIG. 14 uses a different type of fastener for lockingly engaging the proximal nail portion 35 to a correspondingly adapted distal nail portion. As shown in FIG. 14, the socket 35 of the distal nail portion 32 is adapted to receive the clip fastener 36. This is not meant to be limiting, however, as it can be seen how other engaging mechanisms can be substituted for the clip fastener 36 or the set screw (16 of FIG. 1), without departing from the spirit of the invention. Similarly, it can be seen from the present disclosure that other types of mechanisms can be used in place of, or in combination with, the holes 33 or longitudinal slot (13, 23 of FIGS. 1 and 13, respectively) to affix the distal nail portion 32 to a bone, while still keeping with the spirit of the invention.

Figure 6:
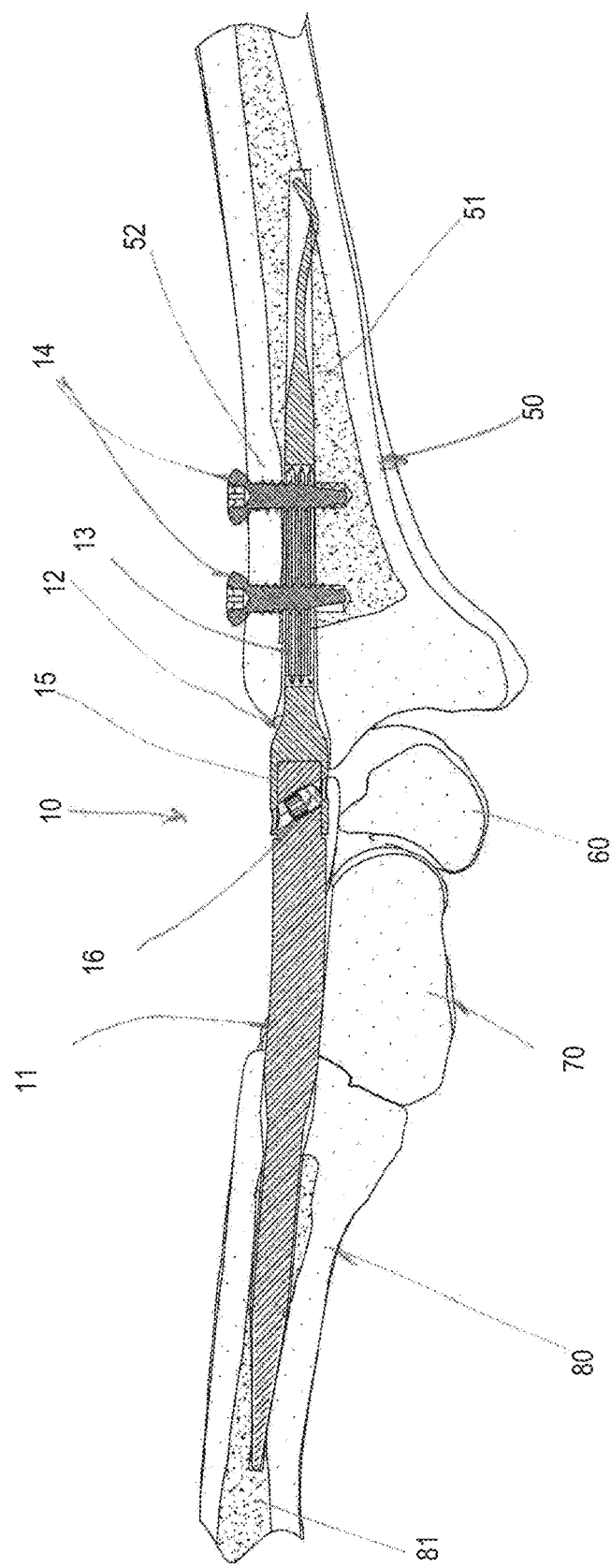
FIG. 6 is a longitudinal cross-sectional view of the intramedullary arthrodesis nail of FIGS. 1, 2 and 3 after it has been surgically installed in a wrist joint.

Referring now to FIG. 6, there is shown one preferred embodiment of an intramedullary arthrodesis nail, in accordance with one embodiment of the present invention, after installation to perform arthrodesis of a wrist joint. As shown in FIG. 6, the distal nail portion 11 has been installed within the medullary cavity 81 of a metacarpal bone 80 (for example, the third metacarpal) and through one of the carpal bones 70 (for example, the capitate). Additionally, the proximal nail portion 12 is installed in the position desired by the surgeon within the medullary cavity 51 of the radius 50, after which the screws 14 are tightened. As a result of the tightening of screws 14, the cortical bone 52 on the dorsal aspect of the radius 50 becomes firmly clamped between the heads of the screws 14 and the upper surface of proximal nail portion 12.

Furthermore, FIG. 6 shows that the set screw 16 has been tightened within the obliquely positioned threaded hole (15b of FIG. 3), resulting in the full engagement of the distal nail portion 11 with the proximal nail portion 12, thereby consolidating the two portions 11, 12 into a rigid structure that will perform as if it were a single, uninterrupted, rigid nail.

The rigid engagement of the intramedullary arthrodesis nail within the radius, carpal and metacarpal bones will lead, with the passage of time, to the fusion of the aforementioned bones resulting in a successful arthrodesis of the wrist while, simultaneously, minimizing the length of the surgical incision, interference with tendons and tenderness at the postoperative site.

Referring now to FIGS. 15A-17 therein is shown a further preferred embodiment of an intramedullary arthrodesis nail of the instant invention. The intramedullary arthrodesis nail 100 includes a distal nail portion 110 intended to be placed, at least partially, within the medullary cavity of at least a first bone and, possibly, a second bone (typically, the third metacarpal and the capitate in the case of the wrist). A plurality of distal nail portions 110 of varying lengths may be provided to accommodate different anatomies.

The distal nail portion 110 preferably includes at least two holes 134 intended to receive screws 141. Holes 134 may be adapted to receive unicortical screws, in which case the holes will be threaded, or bicortical screws, in which case the holes will be unthreaded (shown). The distal nail portion 110 may also include longitudinal slots 130 with two opposing, grooved parallel side walls as further described below in reference to the proximal nail portion in addition to, or instead of, the holes 134. The distal nail portion 110 also includes a distal tail portion 191, an internally splined head portion 150 with at least two splines 152 configured to engage at least one spline of the externally splined portion 171 of a connector 170, 175. Extending through the internally splined head 150 is a threaded hole 154 adapted to receive a set screw 160. In the present embodiment, set screw 160 is chosen to be a correspondingly threaded headless set screw, although other types of screws can be used. As more clearly seen in FIG. 17C, the axis of threaded hole 154 is perpendicular in relation to the longitudinal axis of distal nail portion 110 but may also be oblique to that axis, as desired.

As can more clearly seen in FIG. 16A-16B the connector portions can be straight 170 (i.e., concentrically surrounding an axis extending through the length of the proximal nail portion), curved or angled 175 (i.e., at an angle to the axis extending through the length of the proximal nail portion) and may be provided in a plurality of lengths and curvatures or angles. The connector portions include, at each end, lugs 172 intended to be inserted into heads 150 of distal and proximal nails 110, 120 and to be firmly attached to heads 150 upon tightening of set screws 160. If a straight connector is selected, distal nail 110 and proximal nail 120 will be aligned in the same (neutral) axis; however, if curved or angled connectors are selected the corresponding axes of nail 110 and nail 120 will be at an angle with respect to each other. It should be noted that by rotating the selected curved or angled connectors before inserting the lugs 172 of the connectors into heads 150 of nails 110, 120 the corresponding splines 171 and 152 can be engaged in a plurality of positions. This plurality of positions can be described as a "cone" of possible positions of the axis of distal nail 110 relative to the axis of proximal nail 120.

Referring now to FIGS. 16D-16F there is shown a particular embodiment of the splines 152 in head 150 of distal nail 110 and the corresponding splines 171 of a connector 170. In this particular embodiment there are shown twelve splines 152 in head 150 of distal nail portion 110 and twenty splines 171 in connector portion 170. This differentiation in the number of head splines relative to connector splines is advantageous as it provides more rotational adjustability. If the number of splines in both the head and the connector were identical, for example, twelve in each, the rotational adjustability of the connector relative to the head would be in steps of 30 degrees each. However from any initial position, as illustrated in FIG. 16E, the twenty splines 171 in the connector engage the twelve splines 152 in the head at points a, b, c, d, e, f, g and h. The rotational adjustability of the connector relative to the head is in steps of angle A (in this case, 6 degrees each, instead of 30 degrees) and the new points of engagement of splines 171 in the connector with splines 152 in the head would be at points a', b', c', d', e', f, g' and h' (FIG. 16F). It should be noted that the particular number of splines 152 in the head and 171 in the connector illustrated herein is not intended to be limiting since different number of combinations exist that provide different degrees of rotational adjustment with a corresponding increase or reduction in the number of spline engagement points. The minimum number of splines is two in the head 150 and one in the connector 170 (or vice-versa), which provides engagement but eliminates the rotational adjustability.

Referring again to FIGS. 15A-17, the multi-part intramedullary arthrodesis nail 100 also includes a proximal nail portion 120, intended to be placed, at least partially, within the medullary cavity of at least one other bone of the joint (the radius, in the case of the wrist). The proximal nail portion 120 includes a tail end 190, and an internally splined head portion 150 with at least two splines 152 configured to engage at least one spline of externally splined portion 171 of a connector 170, 175. Extending through the internally splined head 150 is a threaded hole 154 adapted to receive a set screw 160. The proximal nail portion 120 additionally includes at least one longitudinal slot 130 with two opposing, grooved parallel side walls 131 similar to longitudinal slot 13 and grooved parallel side walls 13a described in reference to intramedullary arthrodesis nail 10 of FIGS. 1-5. Preferably, at least 2 grooves on each of the two parallel side walls of longitudinal slot 130 are disposed parallel to the longitudinal axis of proximal nail portion 120 and are configured to match the shape and the pitch of the threads of screws 140. As previously described more particularly in reference to FIG. 5, in this particular embodiment of the instant invention, the grooves 131 on a first side wall of the slot 130 have a vertical displacement of exactly one-half pitch relative to the grooves on the second, opposite side wall of the slot. This relative displacement of opposite side grooves permits the stable engagement of the threads of screws 140 into the side wall grooves of slot 130 at the tangential contact points of the aforementioned threads with the grooves, while still permitting the loosely engaged screws 140 to be displaced horizontally along the length the slots. Complementarily, once the screws are held in a fixed position (for example, by having been inserted into holes drilled in a bone cortex) the slot 130 (and consequently, the totality of proximal nail portion 120) may be displaced longitudinally through a range of positions along the axis of the slots, until such time as the surgeon wishes to fix the proximal nail 120 at a final desired location by further tightening of the screws.

It should be noted that, when screws 140 are tightened by clockwise rotation, such rotation will cause the thread of the screws to pull, draw or lag the grooved longitudinal slot 130 (and consequently, the totality of proximal nail portion 120) towards the heads of the screws. Therefore, any matter, such as a bone cortex, that is interposed between the screw heads and the proximal nail portion 120 will be tightly clamped between the aforementioned screw heads and the upper surface of the nail portion 120.

Referring now to FIGS. 18A-20B, there is shown a multipart drill guide 200 intended to facilitate the installation of an intramedullary arthrodesis nail of the instant invention. In particular, the drill guide 200 is adapted to facilitate the installation of the previously described distal nail 110 (FIGS. 18A, 19A, 20A) and, when flipped about a vertical axis, to facilitate installation of the previously described proximal nail 120 (FIGS. 18B, 19B, 20B) but this is not intended to be limiting, since simple adaptations can be done to drill guide 200 to perform a similar function in relation to other embodiments of the instant invention.

Drill guide 200 is composed of a body portion 201 through which are drilled hole 202, hole 203 and a plurality of holes 204. Each of the holes defines an axis. Upon attachment of drill guide body 201 to either distal nail 110 or proximal nail 120 the axis of each of the holes 202, 203 and 204 is co-planar with and perpendicular to the longitudinal axis of the respective distal nail.

Hole 202 is adapted to receive retention shaft 210. Hole 203 is adapted to receive K-wire 240. Holes 204 are partially open laterally and are adapted to receive, indistinctly, drill sleeve 220 or transfixion pins 230.

Retention shaft 210 is adapted to attach drill guide body 201 to either distal nail 110 or the proximal nail 120. The proximal end of retention shaft 210 has a knob 211 from which projects an extension with two distinct sections 212 and 213 with different external diameters, section 212 having the larger diameter. The distal end of retention shaft 210 is configured to fixedly attach to the head portion 150 of either distal nail 110 or proximal nail 120 by some means such as an external thread congruent with internally threaded hole 154.

K-wire 240 is adapted to temporarily affix proximal nail 120 to one of the bones to be fused (i.e. the radius, in the case of the intramedullary arthrodesis nail for the wrist)

Drill sleeve 220 is adapted to receive a drill bit (not shown) to drill holes in the bones to be fused. Drill sleeve 220 has a cannulated proximal head portion 222, and a cannulated distal extension sleeve 221, attached to each other, coaxially by an eccentric bar 223, A plurality of transfixion pins 230 are cannulated and are adapted to receive K-wires 241 to temporarily affix proximal nail 120 to one of the bones to be fused. The cannulated transfixion pins have a constant internal diameter and include two sections with different external diameters. Section 231 has a larger diameter intended to fit through holes 204 while section 232 has a smaller diameter intended to fit through slot 130 of proximal nail 120.

One particular method for installing the intramedullary arthrodesis nail 10 of FIGS. 1-3 will now be described. Referring now to FIGS. 1-6 and 13-14, to install intramedullary arthrodesis nail, the surgeon approaches the affected wrist through an incision on the dorsal side starting somewhat beyond the proximal articular surface of the selected metacarpal (typically, the articular surface between the third metacarpal and the capitate) and extending proximally to about 6 cms. beyond Lister's tubercle on the dorsal aspect of the distal radius. It should be noted that this incision is about one third to one half of the length required for the installation of a wrist fusion plate.

Placing the wrist in deep flexion, the surgeon drills through the capitate and the third metacarpal, proximal to distal, to prepare for the insertion of the distal nail portion 11 of the intramedullary arthrodesis nail 10. The distal nail 11 is then inserted.

Once the distal nail 11 has been inserted into proper position through the capitate 70 and into the medullary cavity 81 of the metacarpal bone 80, the wrist is manipulated towards a somewhat extended position in such a way that head portion 15a at the proximal end of the distal nail portion 11 points to a location in the distal articular surface of the radius 50 which will become the entry point for placement of the proximal nail portion 12, 22, 32 of the intramedullary arthrodesis nail. The surgeon marks this desired entry point.

The surgeon then drills through the entry point marked in the articular surface of the radius 50 in the direction of the longitudinal medullary cavity 51 of that bone, to prepare for the insertion of the proximal nail portion 12, 22, 32 of the intramedullary arthrodesis nail. With the aid of a jig (not shown) the tail end 17 of the proximal nail portion 12, 22, 32 is inserted through the drilled hole into the medullary cavity 51 of the radius 50.

With the aid of the same jig (not shown), at least two holes are drilled through the dorsal side of the cortical bone 52 of the radius 50 (as illustrated in FIG. 6) to permit the insertion of screws 14 without purchase in the holes. The screws are then engaged loosely into the longitudinal slot 13, but are not yet tightened.

The surgeon then tests the engagement of the head 15a of the distal nail portion 11 in the socket 15, making the necessary adjustment to the longitudinal position of the proximal nail portion 12, 22, 32 by sliding the proximal nail portion 12, 22, 32 back or forth past the loosely engaged screws 14. Once the proximal nail 12, 22, 32 is in the desired position, screws 14 are tightened by rotating them clockwise which action causes dorsal cortical bone 52 to become clamped between the screw heads and the upper surface of the proximal nail portion 12, 22, 32.

The surgeon then selects the desired deviation for the arthrodesis in both the medial-lateral plane and the dorsal-palmar plane. The formable body portion 19 of the distal nail portion 11 is then bent into the proper angles using a bending tool (not shown). Finally, the faceted head 15a of the distal nail portion 11 is inserted into the correspondingly faceted socket 15, 25, 35 of the proximal nail portion 12, 22, 32 and the two nail portions are lockingly affixed to each other by inserting and tightening the set screw 16, thus forming a unitary rigid body of the distal and proximal nail portions. Alternatively, the two nail portions can be affixed with a clip 36, as discussed in connection with FIG. 14. After locking the nail portions together, the incisions are closed by the surgeon in the standard fashion.

Referring now to FIGS. 15-20, one particular method of installing an intramedullary arthrodesis nail 100 will now be described. As with the method described in connection with the intramedullary arthrodesis nail 10 of FIG. 1, the surgeon approaches the affected wrist through an incision on the dorsal side starting somewhat beyond the proximal articular surface of the selected metacarpal (typically, the articular surface between the third metacarpal and the capitate) and extending proximally to about 6 cms beyond Lister's tubercle on the dorsal aspect of the distal radius. The surgeon then exposes the capitate, lunate, distal radius and proximal third metacarpal and decorticates the articular surface of the radiocarpal and intercarpal joints.

The surgeon selects the point of entry for the distal nail 110. This point is in the dorso-radial aspect of the body of the capitate and directly in-line with the medullary canal of the third metacarpal. As needed, the surgeon removes the dorsal aspect of the proximal pole of the scaphoid and the dorsal aspect of the radial border of the lunate in order to provide space to accommodate the distal nail.

The surgeon accesses the medullary canal of the third metacarpal with an awl. Using a K-wire as a probe, the surgeon feels the distal head of the third metacarpal being sure not to penetrate through the end. Proper location of the K-wire in the medullary canal is verified by fluoroscopy. The surgeon reams the medullary canal of the third metacarpal by advancing a cannulated drill over the K-wire. The drill and the K-wire are removed. The surgeon selects an appropriately sized distal nail 110 (i.e. the longest that fits into the third metacarpal).

The distal nail 110 is attached to the drill guide 200 and secured with the retention shaft 210. The distal nail 110 is introduced in to the medullary canal of the third metacarpal until the drill guide 200 seats flush against the body of the capitate.

The drill sleeve is placed through the middle hole 204 of the drill guide. Using a drill bit through the drill sleeve the surgeon creates a hole in the metacarpal and fixes the distal nail 110 to the third metacarpal using screws 141. This process is repeated in the proximal hole 204 of the drill guide. The drill guide 200 is released from the distal nail 110 and removed. The surgeon then selects a connector 170, 175 having a length and angle best suited to the patient's anatomy. A kit including a plurality of connectors having a plurality of lengths and/or angles can be provided. Once the appropriate connector is selected, the lug 172 of the connector 170, 175 is introduced into a channel 151 in the head 150 of the distal nail 110 after adjusting for the desired deviation.

The surgeon places the wrist in the desired functional position and marks the insertion point on the radius as indicated by the end of the opposite lug of the connector. The insertion point is identified by a virtual line running from the distal nail and connector to the medullary canal of the distal radius, traversing over the articular surface of the scaphoid and the lunate. The connector 170, 175 is then removed and the surgeon opens the medullary canal of the distal radius through the marked insertion point with an awl or other device.

The proximal nail 120 is attached and secured to the same drill guide 200 with the retention shaft 210. The proximal nail 120 is inserted into the medullary canal of the radius through the opening and advanced until the drill guide 200 seats flush against the distal articular surface of the radius. The surgeon temporarily affixes the proximal nail to the radius by installing a K-wire 240 through the hole 203 of the drill guide 200. This allows the surgeon to provisionally secure the proximal nail 120 to the radius while performing optimal nail positioning.

The surgeon introduces the drill sleeve 220 through the most distal hole 204 of the drill guide and creates a hole with a drill bit through the near cortex of the radius. The drill sleeve 220 is removed and replaced with a transfixion pin 230. The transfixion pin must transect the slot 130 of proximal nail 120. The surgeon inserts a K-wire 241 through the transfixion pin 230 and stakes it into the far cortex of the radius. This process is repeated to install two additional transfixion pins 230 and K-wires 241. All K-wires 241 are bent towards the open sides of holes 204. The retention shaft and the drill guide 200 are removed, leaving the transfixion pins 230 and all four K-wires in place.

The connector 170, 175 is reinstalled into the distal nail 110 and secured using one of the set screws 160. Pronation and supination may be adjusted by incrementally repositioning the connector around its axes with the distal and proximal nails, using the spline features 151, 172. If using a straight connector, no repositioning is necessary. The connector is then attached to the proximal nail and the correct pronation and supination is reassessed. Once the desired position is achieved, the surgeon applies distal to proximal compression on the connector and installs the other set screw 160 to fix the connector to the proximal nail 120. Both set screws 160 are tightened to firmly affix the connector to the distal nail and the proximal nail, thus forming a unitary rigid body of the connector, distal nail and proximal nail.

The locking K-wire 240 is then removed to allow for compression and distraction of the construct. The proximal nail is then compressed into the radius.

The most distal transfixion pin 230 and its K-wire 241 are removed and a screw 140 is loosely installed in its place. This affixes the proximal nail to the radius.

This process is repeated with for the two remaining transfixion pins. Compression and distraction can still be adjusted by slightly loosening all the screws 140. The surgeon confirms the proper positioning of the wrist arthrodesis nail under fluoroscopy, tightens all the screws, applies bone graft as required and closes the incision.

Figure 7:
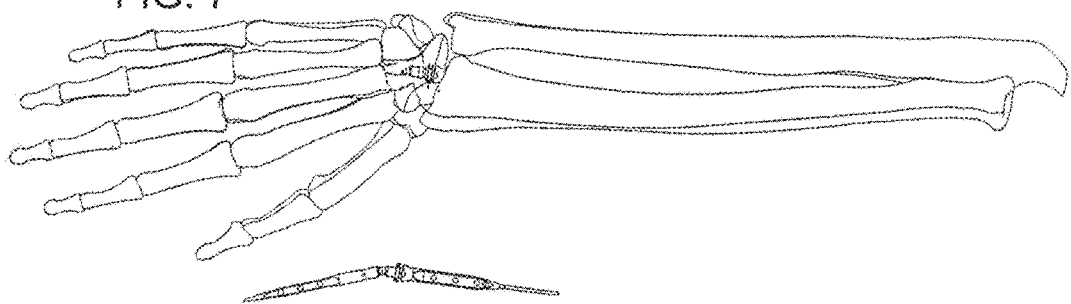
FIGS. 7 thru 9 are plan views of the bones of the hand, wrist and forearm after surgical installation of the intramedullary arthrodesis nail showing various degrees of deviation in the medial-lateral plane.
Figure 8:
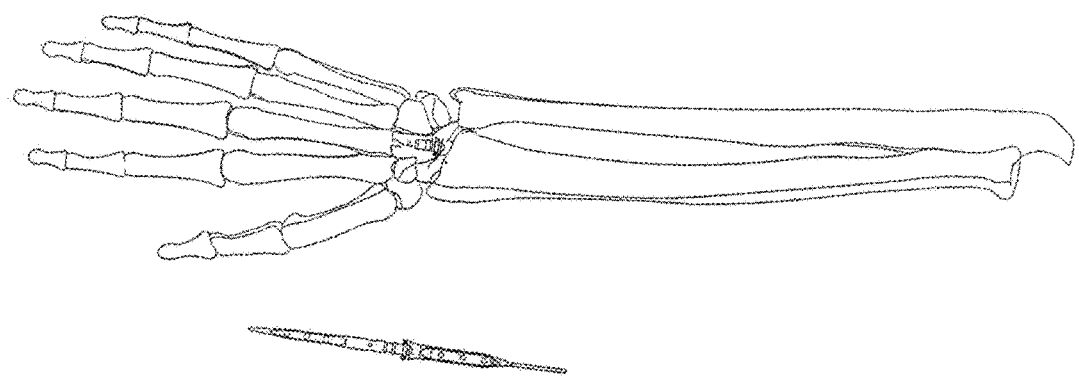
Figure 9:
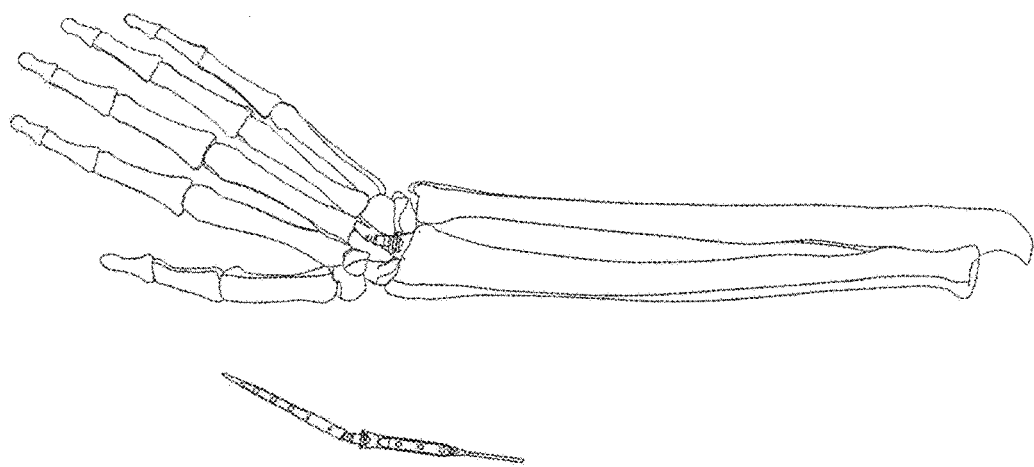
Figure 17A:
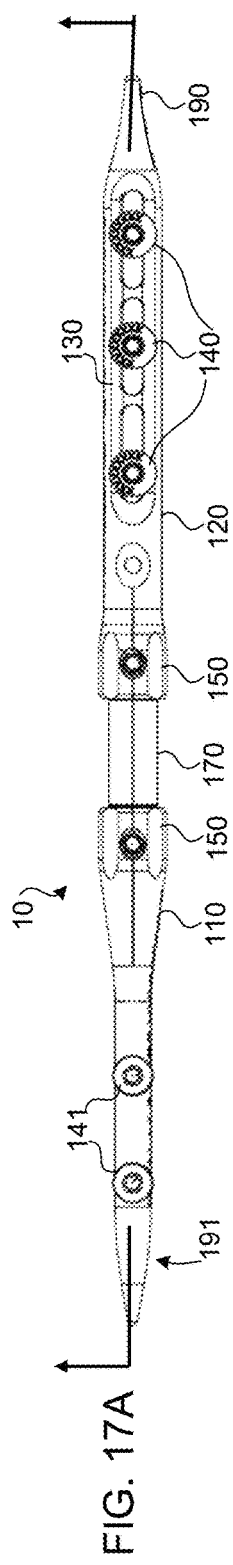
FIGS. 17A-17C are plan, elevational and sectional views of the intramedullary arthrodesis nail of FIG. 15A.
Figure 17B:
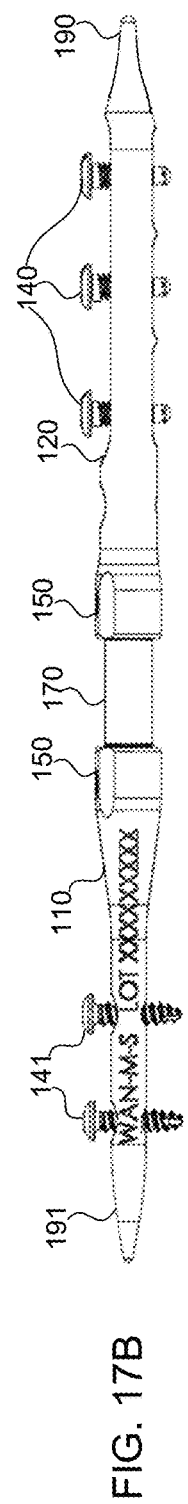
Figure 17C:
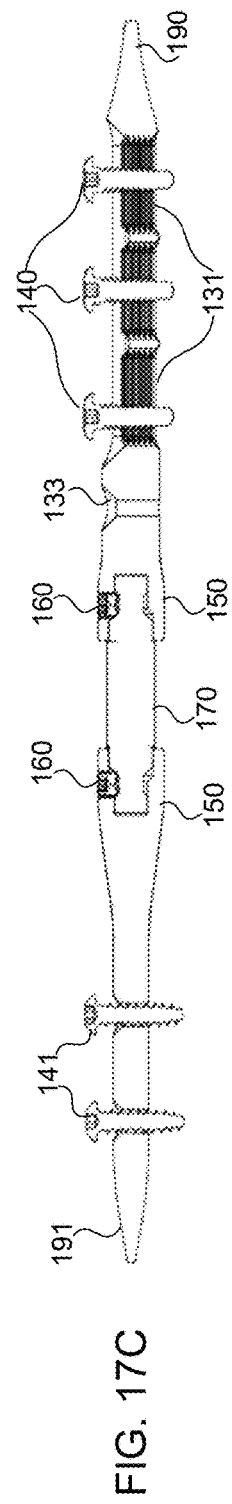
Figure 17D:
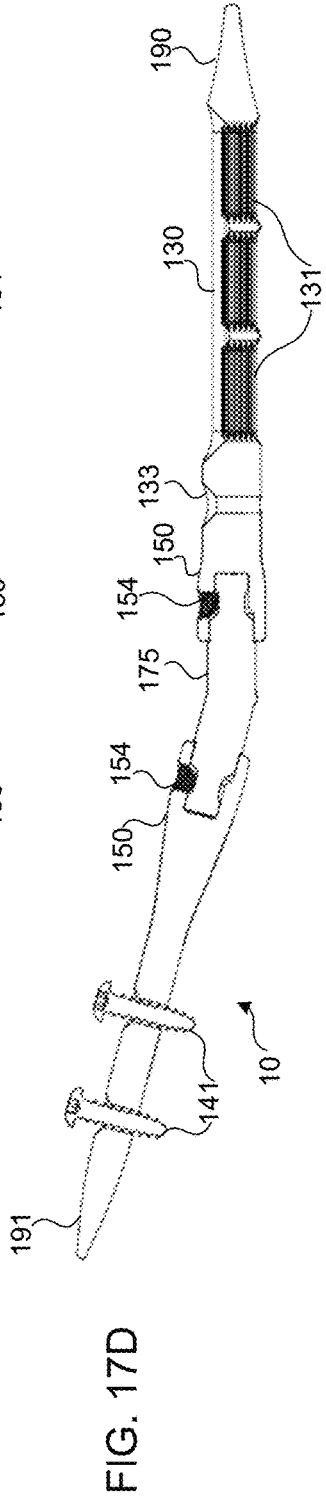
FIG. 17D is a sectional view of another embodiment of an intramedullary nail including the connector of FIG. 16B.
Figures 20A, 20B:
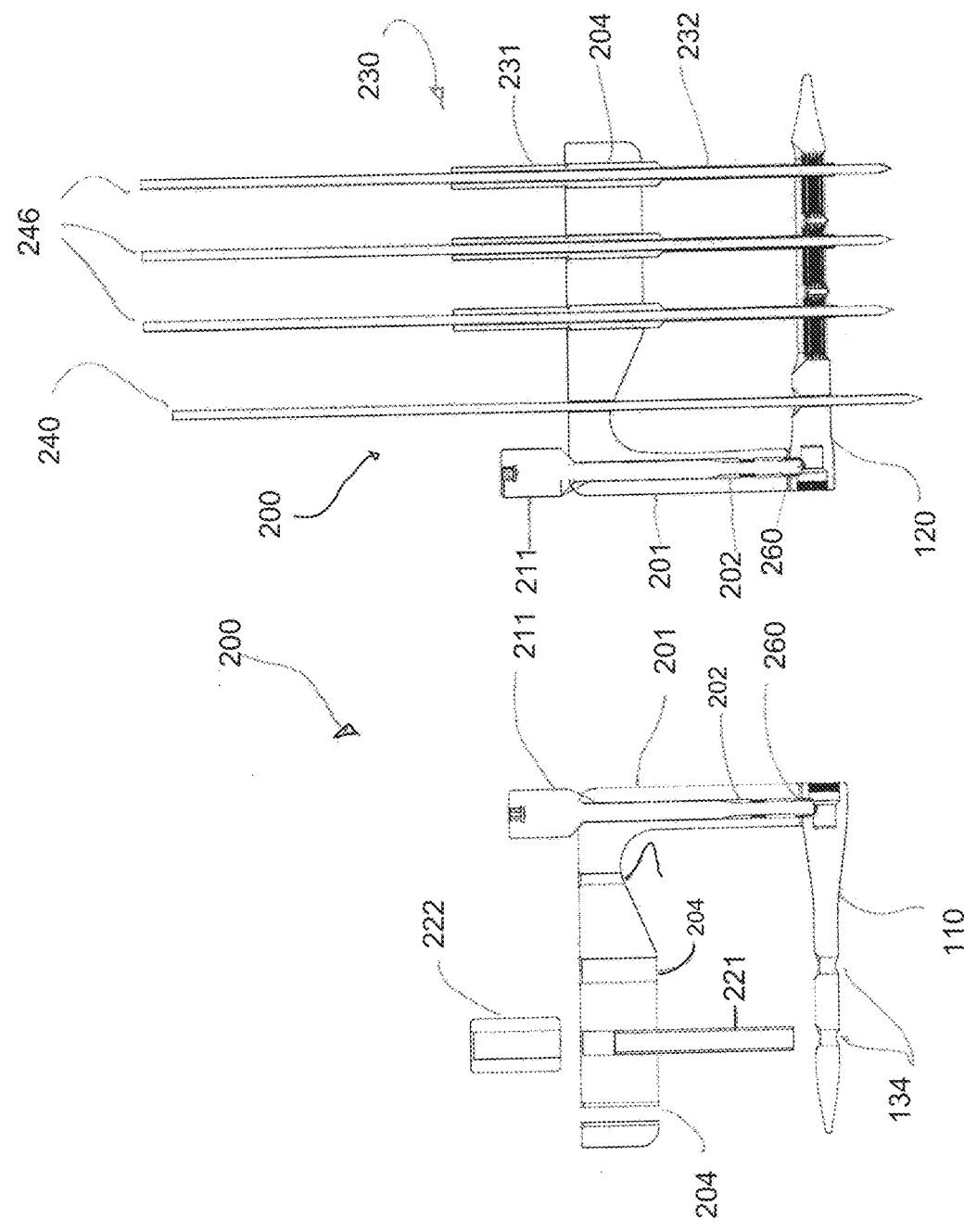
FIGS. 20A and 20B are sectional views of the drill guide and intramedullary arthrodesis nail of FIGS. 19A and 19B, respectively.

FIGS. 7 thru 12 show different examples of the of the many possible intraoperative angle adjustments that can be achieved by bending the formable body portion (19 of FIG. 1) of the distal nail portion (11 of FIG. 1), as described in connection with FIG. 1, as well as by connecting distal nail portion 110 and proximal nail portion 120 with straight connectors or connectors of different curvature or angles as shown in FIGS. 17C and 17D. In particular, FIGS. 7 thru 9 show select examples of various degrees of intraoperative adjustment possible in the lateral-medial plane with FIG. 8 showing a neutral position, while FIGS. 7 and 9 illustrate radial deviation and ulnar deviation of the wrist, respectively.

Figure 10:
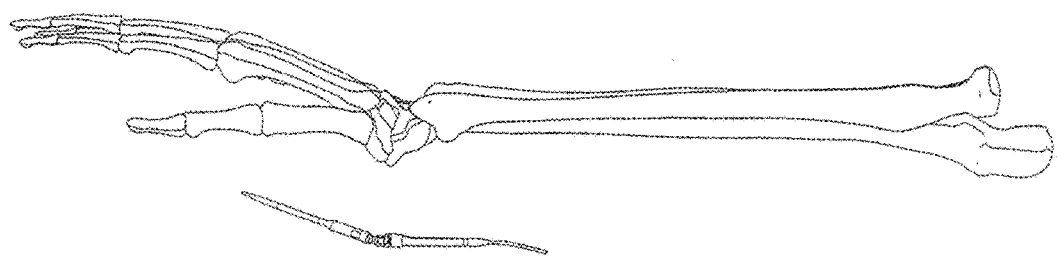
FIGS. 10 thru 12 are side elevational views of the bones of the hand, wrist and forearm after surgical installation of the intramedullary arthrodesis nail showing various degrees of deviation in the palmar-dorsal plane.
Figure 11:
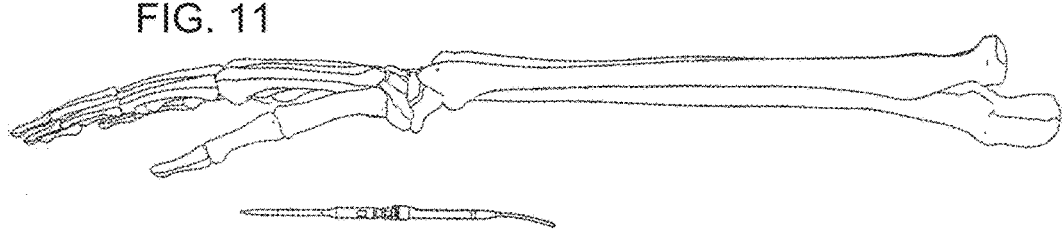
Figure 12:
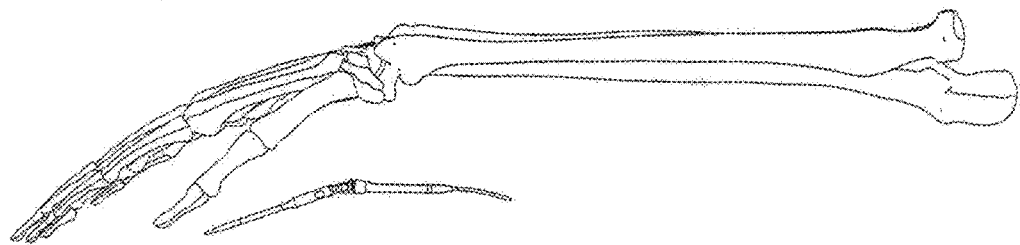

Similarly, FIGS. 10 thru 12 are representative examples of some of the degrees of intraoperative adjustment possible in the palmar-dorsal plane, wherein FIG. 11 shows the neutral position of the device, while FIGS. 10 and 12 illustrate dorsal deviation and palmar deviation of the wrist, respectively.

These adjustments, which can be achieved intraoperatively by bending the formable body portion (19 of FIG. 1) or by choosing straight or angled connectors (170, 175 of FIGS. 17C and 17D respectively) permit the surgeon to obtain, in a simple way, neutrality or optimal deviations of the wrist arthrodesis responding to the needs of the patient. Such deviations would be more difficult, or even impossible, to accomplish with existing plate devices.

Although an intramedullary arthrodesis nail for the wrist has been described above, this is not meant to be limiting. More particularly, it can be seen from the foregoing descriptions how the intramedullary arthrodesis nail described herein can be adapted for other joints of the body by, for example, having a different size or scale, so as to achieve arthrodesis in other joints such as the ankle, the knee or the elbow. As such, although the invention is illustrated and described herein as embodied in a distal nail portion, a proximal nail portion and in, some embodiments, a connector portion, it is nevertheless not intended to be limited to only these details shown, since various modifications and structural changes may be made therein without departing from the spirit of the invention and within the scope and range of equivalents of the claims.

Figure 21:
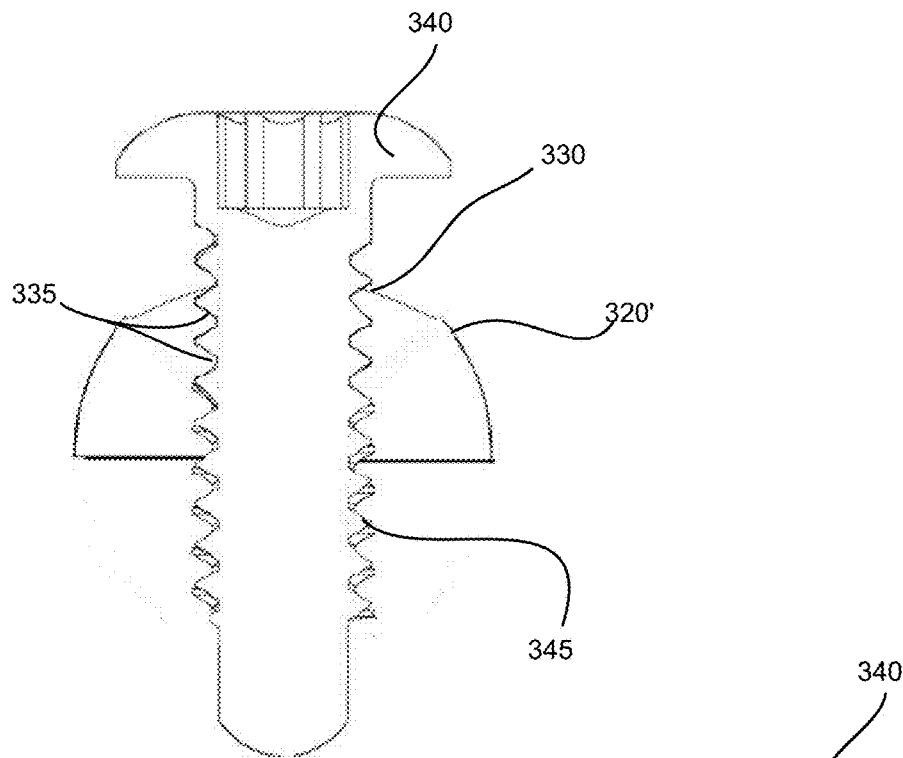
FIG. 21 is a cross-sectional view of a bone fixation device including an elongated, grooved slot and a fastener engaged with the grooves of the slot in accordance with one embodiment of the invention.
Figure 22:
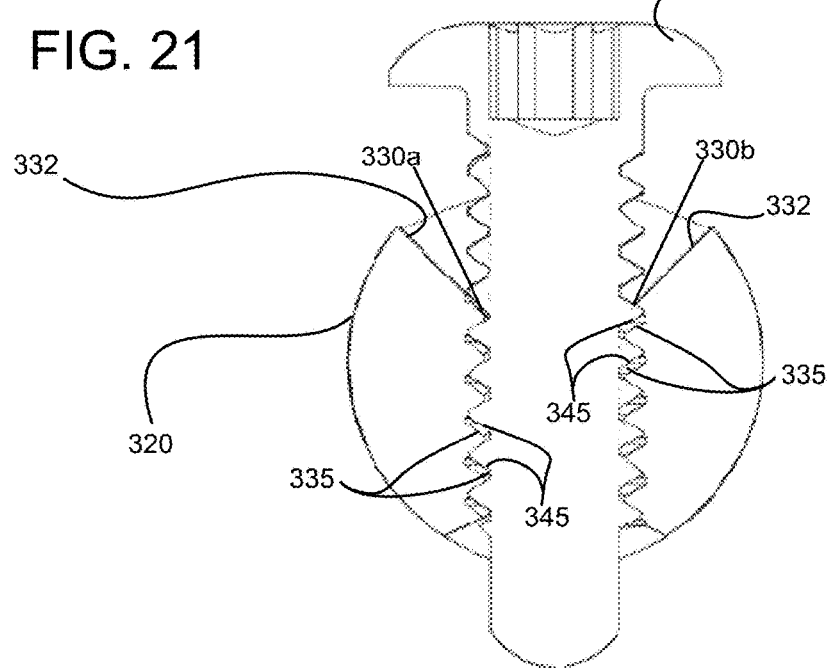
FIG. 22 is a cross-sectional view of a bone fixation device including an elongated, grooved slot and a fastener engaged with the grooves of the slot in accordance with one embodiment of the invention.

The longitudinal slots 13, 130 discussed above, can be used in connection with other types of bone fixation devices, in order to provide ease of installation intraoperatively. For example, referring now to FIGS. 21 and 22, there are illustrated bone fixation devices 320, 320' including a grooved, elongated slot 330 in accordance with the embodiments of the present invention.

More particularly, in the present preferred embodiment, the grooved, elongated slot 330 includes two opposing, grooved parallel side walls which interlock with threads 345 of a fastener 340, which is, in the present embodiment, a bone screw. In the present embodiment, at least two grooves 335 on each of the two parallel side walls of elongated slot 330 are disposed parallel to a longitudinal axis of the bone fixation device 320 and are configured to match the shape and the pitch of the threads 345 of screws 340. Note that, the longitudinal axis of the bone fixation device 320 may be a straight or curved longitudinal axis, depending on the geometry of the bone fixation device 320.

Additionally, in one particular embodiment of the instant invention, the grooves 335 on a first side wall 330a of the elongated slot 330 have a vertical displacement of exactly one-half pitch relative to the grooves 335 on the second, opposite side wall 330b of the slot 330. This relative displacement of opposite side grooves 335 permits the stable engagement of the threads 345 of screws 340 into the side wall grooves 335 of slot 330 at the tangential contact points of the aforementioned threads 345 with the grooves 335, while still permitting the loosely engaged screws 340 to be displaced horizontally to any desired position along the length the slot 330. Complementarily, once the screws are held in a fixed position (for example, by having been inserted into holes drilled in a bone cortex) the slot 330 (and consequently, the totality of the bone fixation device 320, 320') may be displaced longitudinally through a wide range of positions along the slot 330, until such time as the surgeon wishes to fix it at a final desired location by further tightening of the screws.

Referring now to FIGS. 23A-25, there will be described another embodiment of the invention, wherein one or more grooved, elongated slots 430 are used in connection with a bone fixation device for performing osteosynthesis of a fracture of the bone B. In the present embodiment described, bone fixation device 420 is a bone plate made of biocompatible metal (such as titanium, cobalt chrome or stainless steel), PEEK or bio-absorbable material (such as PLA or PGA) or a combination of metal, PEEK and/or bio-absorbable material, and configured to be mounted to the outside surface of a bone B.

Referring again to FIGS. 23A-25, the bone fixation device 420 includes one or more elongated slot 430 with two opposing, grooved parallel side walls 430a and 430b. In a preferred embodiment, at least two grooves 435 on each of the two parallel side walls of elongated slot 430 are disposed in alignment with the longitudinal axis L (which may be straight or curved, based on the geometry of the bone fixation device 420) and are configured to match the shape and the pitch of the threads 445 of screws 440. As shown more particularly in FIG. 25, in one particular embodiment of the instant invention, the grooves 435 on a first side wall 430a of the slot 430 have a vertical displacement of exactly one-half pitch relative to the grooves 435 on the second, opposite side wall 430b of the slot 430. This relative displacement of opposite side grooves 435 permits the stable engagement of the threads 445 of screws 440 into the side wall grooves 435 of slot 430 at the tangential contact points of the aforementioned threads 445 with the grooves 435, while still permitting the loosely engaged screws 440 to be displaced horizontally to any desired position along the length the slot 430. Complementarily, once the screws are held in a fixed position (for example, by having been inserted into holes drilled in a bone cortex) the slot 430 (and consequently, the totality of the bone fixation device 420) may be displaced longitudinally through a wide range of positions along the slot 430, until such time as the surgeon wishes to fix it at a final desired location by further tightening of the screws. Compare, for example, FIGS. 23B, 23C and 24.

Figure 23A:
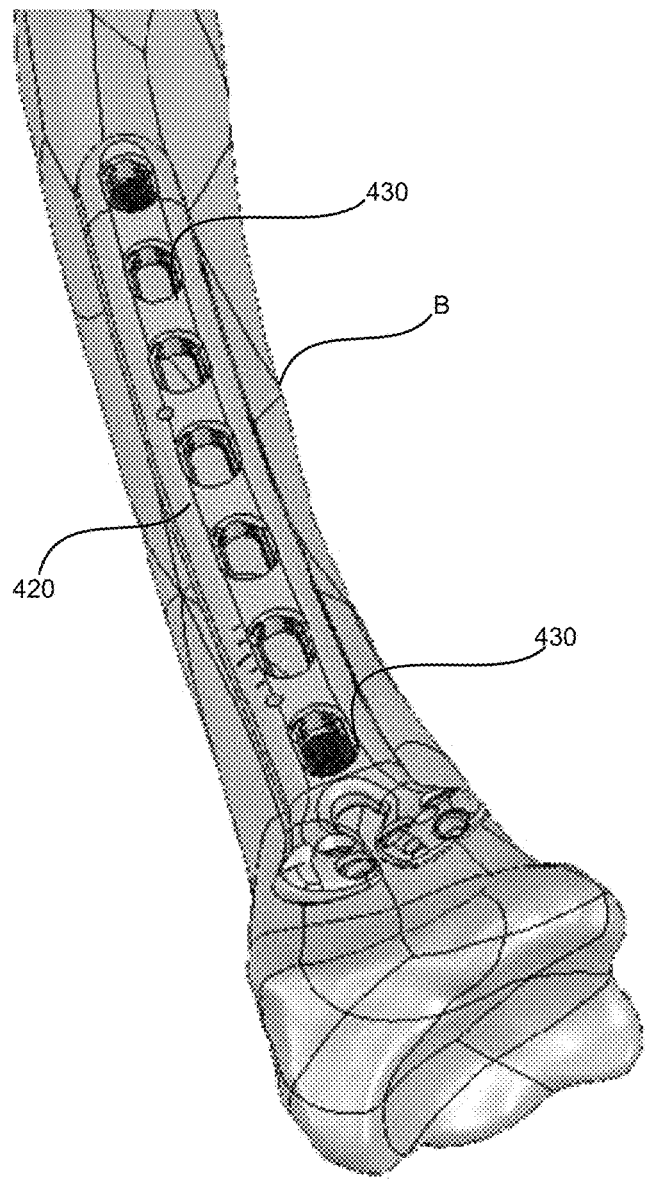
FIG. 23A is a perspective view of a bone having a fracture on which a bone fixation device in accordance with one embodiment of the invention is loosely mounted in a first position.
Figure 23B:
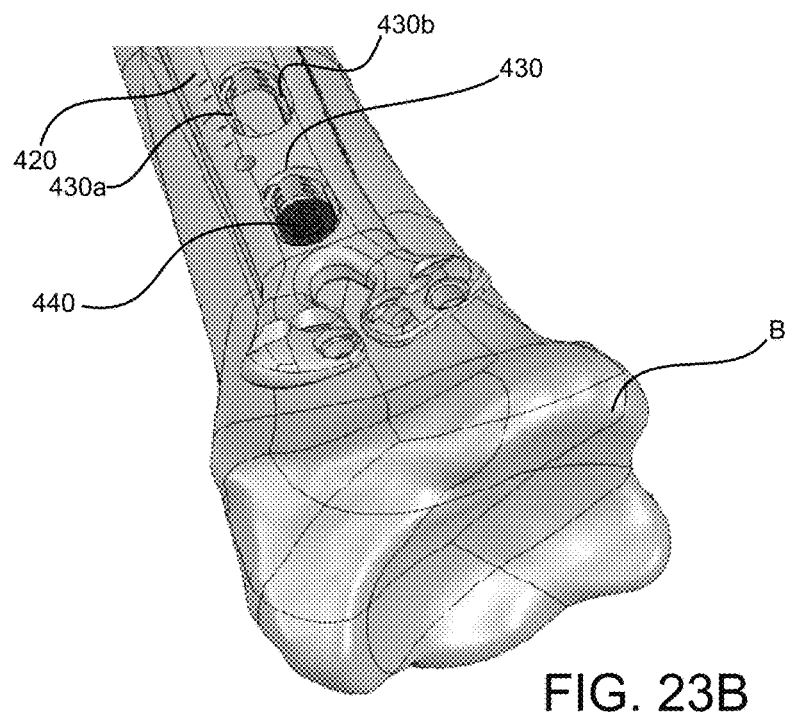
FIG. 23B is a partial, enlarged perspective view of the bone and bone fixation device, in the first position, of FIG. 23A.
Figure 23C:
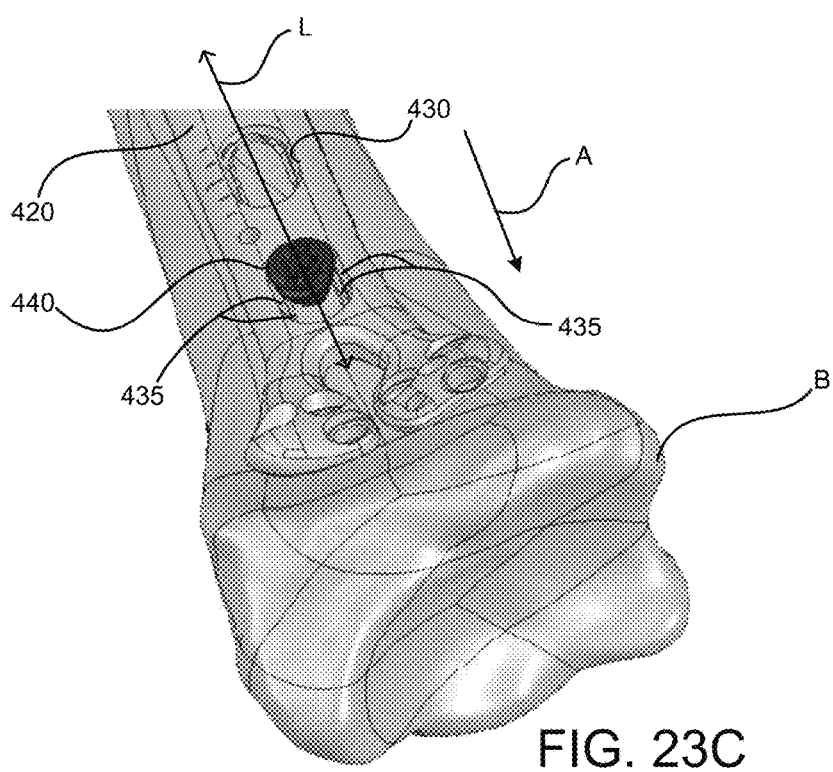
FIG. 23C is a partial, enlarged perspective view of the bone and bone fixation device of FIG. 23A, after the bone fixation device has been moved to a second position, in accordance with one particular embodiment of the invention.

More particularly, as illustrated in FIGS. 23A and 23B, the screw 440 is engaged in the bone B, through the slot 430 at a first position in which the screw is disposed at a first end of the slot, with at least some of the threads 445 engaged with two or more grooves 435 on each sidewall 430a of the elongated slot 430. It should be noted that the ends of each elongated slot 430 are not threaded or grooved in the present embodiment. With the screws 440 fixed to the bone, but loosely engaged within the elongated slot, the bone fixation device 420 can be slid along its longitudinal axis L, to translate the device 420 to another position. In the example illustrated in FIGS. 23A-23C, the bone fixation device 420 is disposed initially with the screw 440 disposed at a first position in the slot 430, but moving the plate in the direction of arrow A displaces the device 420, and correspondingly the slot 430, relative to the fixed screws 440. See also, for example, FIG. 24, wherein the screw is illustrated as being disposed at yet another desired position in the slot 430. Optionally, a scale 405 may be provided on the bone fixation device 420, adjacent the slot 430, to assist the surgeon in positioning the device.

Once the bone fixation device 420 is displaced along the screws 440 to a desired location, the screws can be tightened to lock the head 447 of the screw to the bone fixation device 420, thus preventing further displacement and, consequently, fixing the bone fixation device 420 to the bone at that location. In the embodiments shown, slot 430 is provided with a beveled portion 432 in which the head 447 of the screw can seat (i.e., countersink). More particularly, the device 420 can include a recess 432 at the top edge of the slot 430 so that, once tightened, the head 447 of the screw does not protrude much above the bone fixation device 420.

Figure 24:
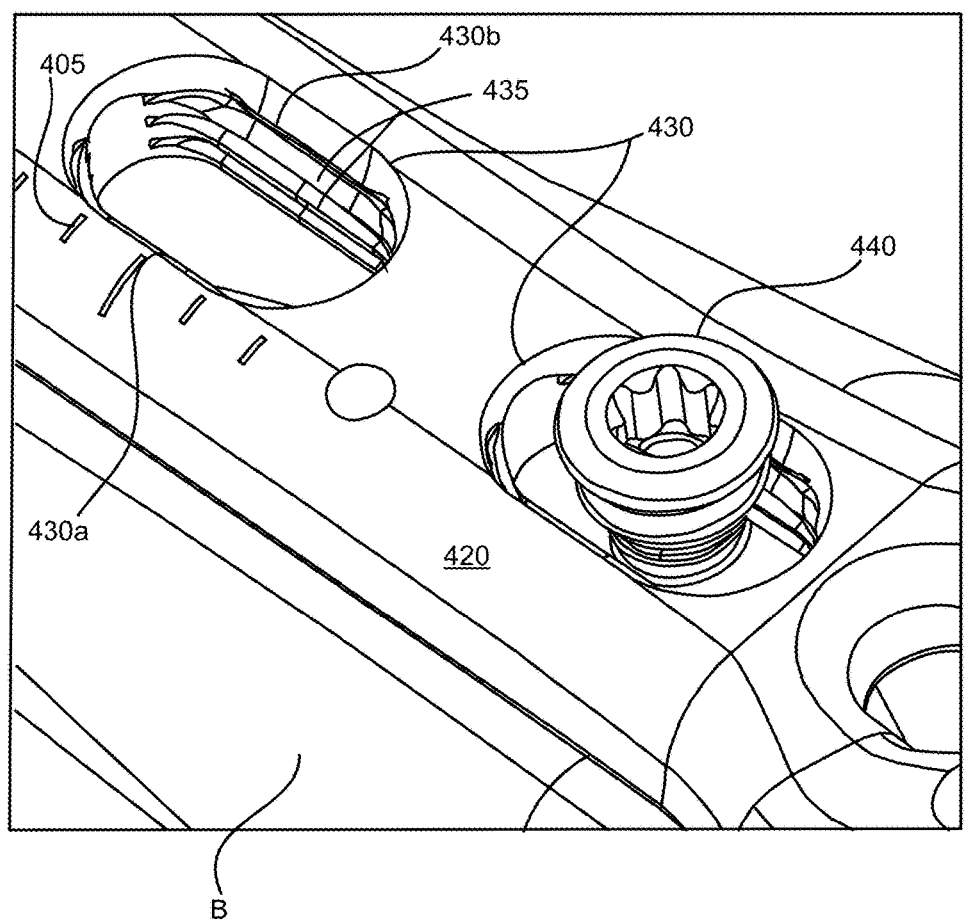
FIG. 24 is a partial, enlarged, perspective view of a bone fixation device including an elongated, grooved slot in accordance with a particular embodiment of the invention.
Figure 25:
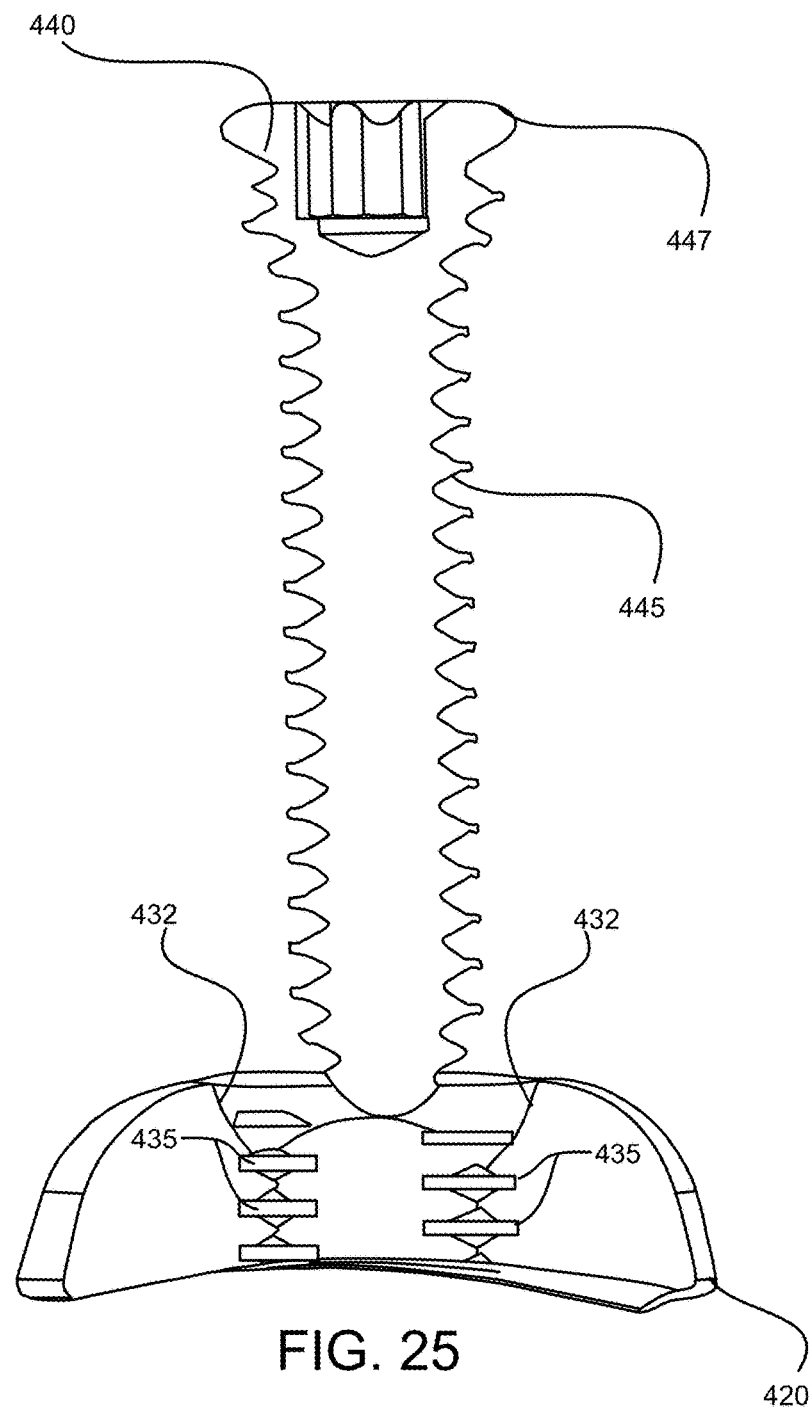
FIG. 25 is a cross-sectional view of an elongated, grooved slot of a bone fixation device for slidably mating with a fastener in accordance with one embodiment of the present invention.

Additionally, in one embodiment of the invention illustrated in FIGS. 24 and 25, to ensure that the head 447 of the screw 440 sits in the recess 432, the head portion is additionally threaded to lock into the parallel grooves of the slot, in order to bring the head 447 into the recess 437. Although the device 420 includes a plurality of apertures therethrough for receiving fasters, as few as one of those apertures, or as many as all of those apertures, may be grooved, and still fall within the scope and spirit of the present invention. Furthermore, some apertures may be circular threaded apertures (not shown) adapted to accept additional screws 440 to be inserted and locked into the bone fixation device after it has been placed in a desired location, to further secure the construct.

Although a particular example of an elongated slot in a bone fixation device has been described above, this is not intended to be limited to only these details shown, since various modifications and structural changes may be made therein without departing from the spirit of the invention and within the scope and range of equivalents of the claims.

What is claimed is:

1. An elongated bone fixation device for osteosynthesis, defining a longitudinal axis and configured to receive one or more fasteners in apertures therethrough for positioning the device relative to a bone, at least one fastener having a thread defining a shape and a pitch, the elongated bone fixation device, comprising:
    at least one aperture configured as an elongated slot extending through the bone fixation device, said elongated slot configured to receive the at least one fastener from a top of the slot;
    said elongated slot including two opposing, grooved parallel side walls and two ungrooved walls enclosing said slot at each end, the grooves on each of said parallel side walls having a shape and a pitch configured to match the shape and pitch of the thread of the fastener, all of said grooves being disposed parallel to each other; and
    wherein the grooves on a first of said parallel side walls are vertically displaced one-half of said pitch relative to the grooves on the second, opposite, side wall to permit the bone fixation device to be displaced longitudinally along said slot when the at least one threaded fastener is first engaged into a cortex of a bone through the top of said slot, and to fix the bone fixation device relative to the bone when the fastener is further tightened such that the threads of the fastener are fully engaged with said grooves.

2. The elongated bone fixation device of claim 1, wherein the bone fixation device is an intramedullary nail.

3. The elongated bone fixation device of claim 1, wherein the bone fixation device is a bone plate.

4. The elongated bone fixation device of claim 1, wherein the at least one elongated slot is at least two elongated slots.

5. The elongated bone fixation device of claim 1, wherein at least one elongated slot is aligned with the longitudinal axis of the bone fixation device.

6. The elongated bone fixation device of claim 1, wherein at least one aperture is configured as a circular threaded aperture.

7. The elongated bone fixation device of claim 1, wherein at least one elongated slot is aligned with the longitudinal axis of the bone fixation device.

8. The elongated slot according to claim 7, wherein all of said grooves are disposed parallel to the longitudinal axis of the bone fixation device.

9. A method for performing osteosynthesis, comprising the steps of:
    providing a bone fixation device according to claim 1;
    placing the bone fixation device into an initial position relative to a bone;
    inserting a threaded fastener through the elongated slot into a cortex of a bone;
    adjusting the position of the bone fixation device relative to the bone after the inserting step; and
    after the adjusting step, tightening the threaded fastener into a locked position relative to the elongated slot to fix the bone fixation device relative to the bone.

10. An elongated slot formed in a bone fixation device for osteosynthesis, and configured to receive one or more fasteners from a top of the elongated slot therethrough for positioning the bone fixation device relative to a bone, at least one fastener having a thread defining a shape and a pitch, the elongated slot, comprising:
    two opposing, grooved parallel side walls, the grooves on each of said parallel side walls having a shape and a pitch configured to match the shape and pitch of the thread of the fastener, all of said grooves being disposed parallel to each other;
    two ungrooved walls enclosing said slot at each end, wherein said two grooved side walls are longer than the two ungrooved end walls; and
    wherein the grooves on a first of said parallel side walls are vertically displaced one-half of said pitch relative to the grooves on the second, opposite, side wall to permit the bone fixation device to be displaced longitudinally along said slot when the at least one threaded fastener is first engaged into a cortex of a bone through the top of said slot, and to fix the bone fixation device relative to the bone when the fastener is further tightened such that the threads of the fastener are fully engaged with said grooves.

11. The elongated slot of claim 10, wherein the bone fixation device is an intramedullary nail.

12. The elongated slot of claim 10, wherein the bone fixation device is a bone plate.

13. A device comprising a body for fixation to a bone by threaded screws, the threaded screws having a thread shape and a thread pitch, the body comprising:
- at least one slot extending through a thickness of the body in a vertical direction, the slot having a length extending along an axis of the body and a width extending between first and second opposed parallel sidewalls, the first and second sidewalls spaced apart from each other to receive at least one of said threaded screws therebetween, said slot additionally including two ungrooved walls enclosing said slot at each end, wherein said two grooved side walls are longer than the two ungrooved end walls, and the length of the slot is greater than the width to accommodate axial adjustment of the body relative to said at least one threaded screw prior to fully tightening the screw;
- wherein each of the first and second sidewalls includes at least two grooves extending parallel to the axis, the grooves each having a groove shape configured to receive the thread shape of a tangential portion of the screw in threaded engagement, and
- wherein the grooves of each sidewall are spaced apart in the vertical direction by a vertical spacing equal to the thread pitch, and the grooves of the first sidewall are displaced in the vertical direction one-half of the thread pitch relative to the grooves of the second sidewall.

* * * * *